US011197722B2

(12) United States Patent
Tako et al.

(10) Patent No.: US 11,197,722 B2
(45) Date of Patent: Dec. 14, 2021

(54) SURGICAL NAVIGATION INSIDE A BODY

(71) Applicant: Surgical Theater, Inc., Los Angeles, CA (US)

(72) Inventors: Yahav Tako, New York, NY (US); Alon Yakob Geri, Beachwood, OH (US); Mordechai Avisar, Highland Heights, OH (US); Eliahu Teichman, Byniamina (IL)

(73) Assignee: SURGICAL THEATER, INC., Los Angeles, CA (US)

( * ) Notice: Subject to any disclaimer, the term of this patent is extended or adjusted under 35 U.S.C. 154(b) by 0 days.

(21) Appl. No.: 15/699,715

(22) Filed: Sep. 8, 2017

(65) Prior Publication Data

US 2017/0367771 A1 Dec. 28, 2017

Related U.S. Application Data

(63) Continuation-in-part of application No. PCT/US2016/056727, filed on Oct. 13, 2016.
(Continued)

(51) Int. Cl.
*A61B 34/20* (2016.01)
*G06T 19/00* (2011.01)
(Continued)

(52) U.S. Cl.
CPC ............ *A61B 34/20* (2016.02); *G06T 19/003* (2013.01); *A61B 2034/105* (2016.02);
(Continued)

(58) Field of Classification Search
CPC ..... G06T 19/006; G06T 19/003; A61B 34/20; A61B 2090/365
See application file for complete search history.

(56) References Cited

U.S. PATENT DOCUMENTS

| 5,595,703 A | 1/1997 | Swaelens et al. |
| 5,768,134 A | 6/1998 | Swaelens et al. |

(Continued)

FOREIGN PATENT DOCUMENTS

| CN | 1720561 A | 1/2006 |
| CN | 1973780 A | 6/2007 |

(Continued)

OTHER PUBLICATIONS

Ferrari, Vincenzo, et al. "A 3-D mixed-reality system for stereoscopic visualization of medical dataset." IEEE Transactions on Biomedical Engineering 56.11 (2009): 2627-2633. (Year: 2009).*
(Continued)

*Primary Examiner* — Daniel F Hajnik
(74) *Attorney, Agent, or Firm* — Bodi Law LLC

(57) ABSTRACT

A virtual reality surgical navigation method includes the steps of preparing a multi dimension virtual model associated with an anatomy inside of patient; receiving data indicative of a surgeon's current head position, including direction of view and angle of view; rendering a first virtual three-dimensional image from the virtual model, the virtual three-dimensional image being representative of an anatomical view from a first perspective at a location inside the patient, wherein the perspective is determined by data indicative of the surgeon's current head position; communicating the first rendered virtual image to a virtual headset display; receiving data input indicative of the surgeon's head moving to a second position, wherein the head movement comprises at least one of a change in angle of view and a change in direction of view; and rendering a second virtual three-dimensional image from the virtual model, the second virtual three-dimensional image being representative of an anatomical view from a second perspective at a first location inside the patient.

49 Claims, 34 Drawing Sheets

Related U.S. Application Data

(60) Provisional application No. 62/241,447, filed on Oct. 14, 2015.

(51) Int. Cl.
*A61B 90/00* (2016.01)
*A61B 34/10* (2016.01)
*A61B 90/50* (2016.01)

(52) U.S. Cl.
CPC ... *A61B 2090/365* (2016.02); *A61B 2090/372* (2016.02); *A61B 2090/502* (2016.02); *G06T 2210/41* (2013.01); *G06T 2210/62* (2013.01)

(56) References Cited

U.S. PATENT DOCUMENTS

| | | |
|---|---|---|
| 5,826,206 A | 10/1998 | Nemeth |
| 6,037,927 A | 3/2000 | Rosenberg |
| 6,113,395 A | 9/2000 | Hon |
| 6,847,336 B1 | 1/2005 | Lemelson et al. |
| 6,857,878 B1 | 2/2005 | Chosack et al. |
| 6,863,536 B1 | 3/2005 | Fisher et al. |
| 6,939,138 B2 | 9/2005 | Chosack et al. |
| 7,101,383 B1 | 9/2006 | Van Ess |
| 7,261,565 B2 | 8/2007 | Chosack et al. |
| 7,616,730 B2 | 11/2009 | Flohr |
| 8,311,791 B1 | 11/2012 | Avisar |
| 8,504,136 B1 | 8/2013 | Sun et al. |
| 9,788,905 B2 | 10/2017 | Avisar |
| 10,056,012 B2 | 8/2018 | Geri et al. |
| 2001/0046935 A1 | 11/2001 | Okamura |
| 2002/0059284 A1 | 5/2002 | Bronstein et al. |
| 2004/0253572 A1 | 12/2004 | Chosack et al. |
| 2005/0032028 A1 | 2/2005 | Chosack et al. |
| 2006/0036167 A1 | 2/2006 | Shina |
| 2006/0082542 A1 | 4/2006 | Morita et al. |
| 2006/0085175 A1 | 4/2006 | Hartlep et al. |
| 2006/0276708 A1* | 12/2006 | Peterson ............... A61B 5/055 600/416 |
| 2006/0281971 A1 | 12/2006 | Sauer |
| 2007/0129626 A1 | 6/2007 | Mahesh et al. |
| 2007/0134637 A1 | 6/2007 | Bronstein et al. |
| 2007/0141543 A1 | 6/2007 | Grund-Pedersen |
| 2007/0236514 A1* | 10/2007 | Agusanto ........... A61B 1/00193 345/646 |
| 2007/0248261 A1 | 10/2007 | Zhou et al. |
| 2009/0018808 A1 | 1/2009 | Bronstein et al. |
| 2009/0187393 A1 | 7/2009 | Van Lierde et al. |
| 2009/0311655 A1 | 12/2009 | Karkanias et al. |
| 2010/0009314 A1 | 1/2010 | Tardieu et al. |
| 2010/0092904 A1 | 4/2010 | Esposti et al. |
| 2010/0161076 A1 | 6/2010 | Pallari |
| 2010/0178644 A1 | 7/2010 | Meglan et al. |
| 2010/0191088 A1 | 7/2010 | Anderson et al. |
| 2010/0217336 A1 | 8/2010 | Crawford et al. |
| 2010/0305928 A1 | 12/2010 | Cohen et al. |
| 2011/0236868 A1 | 9/2011 | Bronstein et al. |
| 2011/0238395 A1 | 9/2011 | Kubota et al. |
| 2012/0041318 A1* | 2/2012 | Taylor ................. A61B 6/503 600/504 |
| 2012/0058457 A1 | 3/2012 | Savitsky |
| 2013/0047103 A1 | 2/2013 | Avisar |
| 2013/0267838 A1 | 10/2013 | Fronk et al. |
| 2014/0088941 A1* | 3/2014 | Banerjee ............. G06F 3/011 703/11 |
| 2014/0176661 A1 | 6/2014 | Smurro et al. |
| 2014/0243614 A1* | 8/2014 | Rothberg ............. A61B 8/13 600/301 |
| 2014/0275760 A1 | 9/2014 | Lee |
| 2015/0002541 A1* | 1/2015 | Dillavou ............. G06T 19/006 345/633 |
| 2015/0062157 A1* | 3/2015 | Dragnea ............. G06T 19/006 345/633 |
| 2015/0248793 A1* | 9/2015 | Abovitz ............. G06K 9/00671 345/633 |
| 2016/0022125 A1* | 1/2016 | Nicolau ............... A61B 5/062 600/424 |
| 2016/0027141 A1* | 1/2016 | Patel ................... G06T 1/20 345/522 |
| 2016/0143699 A1* | 5/2016 | Tanji ................... A61B 34/20 600/431 |
| 2016/0154620 A1* | 6/2016 | Tsuda ................. G06F 19/3481 345/633 |
| 2018/0092698 A1 | 4/2018 | Chopra et al. |

FOREIGN PATENT DOCUMENTS

| | | |
|---|---|---|
| CN | 102354345 A | 2/2012 |
| EP | 1 395 194 A1 | 3/2004 |
| EP | 3 146 715 A1 | 3/2017 |
| EP | 3 280 344 A2 | 2/2018 |
| JP | 2006509238 A | 3/2006 |
| JP | 2006223374 | 8/2006 |
| JP | 2010131047 | 6/2010 |
| JP | 2014522248 | 9/2014 |
| JP | 2014525764 | 10/2014 |
| WO | WO9610949A1-1 | 4/1996 |
| WO | WO9610949A1-2 | 4/1996 |
| WO | WO 02/100284 A1 | 12/2002 |
| WO | 2004029908 A1 | 4/2004 |
| WO | 2004051603 A1 | 6/2004 |
| WO | WO2004051603 A | 6/2004 |
| WO | WO 2008/076079 | 6/2008 |
| WO | 2009059716 A1 | 5/2009 |
| WO | O2009059716 A1 | 5/2009 |
| WO | 2009094621 A2 | 7/2009 |
| WO | 2010030523 A1 | 3/2010 |
| WO | WO2010106532 A1 | 9/2010 |
| WO | 2010132606 A1 | 11/2010 |
| WO | 2012/033739 A1 | 3/2012 |
| WO | 2012135653 A1 | 10/2012 |
| WO | 2013177520 A1 | 11/2013 |
| WO | WO 2015/008470 A2 | 1/2015 |
| WO | 2015154069 A1 | 10/2015 |

OTHER PUBLICATIONS

Bichlmeier, Christoph, et al. "Contextual anatomic mimesis hybrid in-situ visualization method for improving multi-sensory depth perception in medical augmented reality." Mixed and Augmented Reality, 2007. ISMAR 2007. 6th IEEE and ACM International Symposium on. IEEE, 2007. (Year: 2007).*

NPL Video titled "3D Visualizer with Oculus and Hydra", Published by okreylos on Aug. 15, 2013; https://www.youtube.com/watch?v=MWGBRsV9omw; select screenshots included. (Year: 2013).*

NPL Video titled "EON Reality—Human Anatomy Builder", Published by EON Reality on Mar. 10, 2015; https://www.youtube.com/watch?v=oFTO4KgccTY; select screenshots included. (Year: 2015).*

Montgomery, K. et al; Studies in Health Technology and Informatics; "Spring: A General Framework for Collaborative, Real-time Surgical Simulation"; 2002, vol. 85, pp. 296-303.

Qin, J. et al; Studies in Health Technology and Informatics; "An Adaptive Framework Using Cluster-Based Hybrid Architecture for Enhancing Collaboration in Surgical Simulation"; 2007, vol. 125, pp. 367-372.

Joanna Leng; Scientific Examples of Virtual Reality and Visualization Applications; Manchester Research Center for Computational Science; Mar. 2001; part "Surgical Simulation"; No Copy Attached.

M.A. Padilla et al., Computer Simulation of Prostate Surgery; Universidad Nacional Automoma de Mexico; Oct. 15, 2007; No Copy Attached.

J Neurosurg vol. 93; Relevant Pages: pp. 355-369 and Figures 3, 4, 6 and 8; Date of Issuance: Aug. 31, 2000; Title of Article: "Simulation of the surgical manipulation involved in clipping a basilar artery aneurysm: concepts of virtual clipping"; Author and Publisher: Toru Koyama, M.D. et al.; Department of Neurosurgery, Shinshu University School of Medicine Matsumoto, Japan.

(56) References Cited

OTHER PUBLICATIONS

MedGadget (Surgical Navigation Advanced Platform (SNAP) for Intra-Op Visualization of Patient's Brain, https://www.medgadget.co m/2014/07 /surg i cal-n avigation-advanced-platfor msnap-for-intra-op-visual izati on-of-patients-brain. ht ml, Jul. 3, 2014).

Bornik A et al: "Computer Aided Liver Surgery Planni ng: An Augmented Reality Approach" Visual Communications and Image Processing; vol. 5029, Feb. 15, 2003, pp. 395-406.

Reitinger, et al: "Liver Surgery Planning Using Virtual Reality"; Virtual and Augmented Reality Supported Similators; IEEE Computer Society; Nov./Dec. 2006.

\* cited by examiner

SURGICAL NAVIGATION INSIDE A BODY

CROSS-REFERENCES TO RELATED APPLICATIONS

This application is a continuation-in-part of PCT Application No. PCT/US2016/056727 filed on Oct. 13, 2016, which claims the benefit of U.S. Provisional Application Ser. No. 62/241,447 which was filed on Oct. 14, 2015 both of which are incorporated herein by reference.

BACKGROUND

Surgical procedures may often be complex and time sensitive and vary in scope from one patient to another. For example, in the case of an aneurysm repair, the point of repair may vary in terms or procedural requirements depending on the exact location, size, and so on. Therefore, the efficiency of the procedure is highly critical and detailed planning based on the patient specific local geometry and physical properties of the area on which surgery is being performed is fundamental. To achieve a new level of pre-surgery preparation, 3D CT and MRI images are being increasingly utilized. However, those images offer only minor benefits, standing alone, for surgery rehearsal. Moreover, existing techniques for studying a patient's specific anatomy prior to or during surgery may be invasive to the patient.

A surgery rehearsal and preparation tool previously described in U.S. Pat. No. 8,311,791, incorporated herein by reference, has been developed to convert static medical images into dynamic and interactive multi-dimensional full spherical virtual reality, six (6) degrees of freedom models ("MD6DM") that can be used by physicians to simulate medical procedures in real time.

In one example, a physician may want to leverage the information available in the MD6DM and use it during an actual surgery procedure inside an operating room (OR). However, a surgeon may already be using a microscope or an endoscope in the operating room during a procedure. Thus, it may be inefficient, distracting, and time consuming for the surgeon to take his eyes off the microscope or endoscope to look at the MD6DM or other types of patient scans or data. In addition, including additional equipment and systems for viewing patient scans and models such as MD6DM in an already crowded operating room may not be practical or possible.

Also, in addition to simulating a medical procedure, it may also be desirable to efficiently navigate a patient's anatomy non-invasively, using such 3D CT and MRI imagery, prior to or during a surgical procedure in order to enable timely and accurate completion of the surgical procedure.

SUMMARY

A virtual reality surgical navigation system includes one or more processors, one or more computer-readable tangible storage devices, and program instructions stored on at least one of the one or more storage devices for execution by at least one of the one or more processors. The program instructions include first program instructions for preparing a multi dimension virtual model associated with an anatomy inside of patient. The program instructions further include second program instructions for receiving data indicative of a surgeon's current head position, including direction of view and angle of view. The program instructions further include third program instructions for rendering a first virtual three-dimensional image from the virtual model, the virtual three-dimensional image being representative of an anatomical view from a first perspective at a location inside the patient, wherein the perspective is determined by data indicative of the surgeon's current head position. The program instructions further include fourth program instructions for communicating the first rendered virtual image to a virtual headset display. The program instructions further include fifth program instructions for receiving data input indicative of the surgeon's head moving to a second position, wherein the head movement comprises at least one of a change in angle of view and a change in direction of view. The program instructions further include sixth program instructions for rendering a second virtual three-dimensional image from the virtual model, the second virtual three-dimensional image being representative of an anatomical view from a second perspective at a first location inside the patient.

A computer program product comprising one or more computer-readable tangible storage devices, and program instructions stored on at least one of the one or more storage devices. The program instructions include first program instructions for preparing a multi dimension virtual model associated with an anatomy inside of patient. The program instructions further include second program instructions for receiving data indicative of a surgeon's current head position, including direction of view and angle of view. The program instructions further include third program instructions for rendering a first virtual three-dimensional image from the virtual model, the virtual three-dimensional image being representative of an anatomical view from a first perspective at a location inside the patient, wherein the perspective is determined by data indicative of the surgeon's current head position. The program instructions further include fourth program instructions for communicating the first rendered virtual image to a virtual headset display. The program instructions further include fifth program instructions for receiving data input indicative of the surgeon's head moving to a second position, wherein the head movement comprises at least one of a change in angle of view and a change in direction of view. The program instructions further include sixth program instructions for rendering a second virtual three-dimensional image from the virtual model, the second virtual three-dimensional image being representative of an anatomical view from a second perspective at a first location inside the patient.

A virtual reality surgical navigation method includes the step of preparing a multi dimension virtual model associated with an anatomy inside of patient. The method further includes the step of receiving data indicative of a surgeon's current head position, including direction of view and angle of view. The method further includes the step of rendering a first virtual three-dimensional image from the virtual model, the virtual three-dimensional image being representative of an anatomical view from a first perspective at a location inside the patient, wherein the perspective is determined by data indicative of the surgeon's current head position. The method further includes the step of communicating the first rendered virtual image to a virtual headset display. The method further includes the step of receiving data input indicative of the surgeon's head moving to a second position, wherein the head movement comprises at least one of a change in angle of view and a change in direction of view. The method further includes the step of rendering a second virtual three-dimensional image from the virtual model, the second virtual three-dimensional image being representative of an anatomical view from a second perspective at a first location inside the patient.

Also provided are additional example embodiments, some, but not all of which, are described herein below in more detail.

BRIEF DESCRIPTION OF THE DRAWINGS

The patent or application file contains at least one photograph executed in black and white. Copies of this patent or patent application publication with black and white photograph drawings will be provided by the Office upon request and payment of the necessary fee. In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION OF THE EXAMPLE EMBODIMENTS

Figure 1:
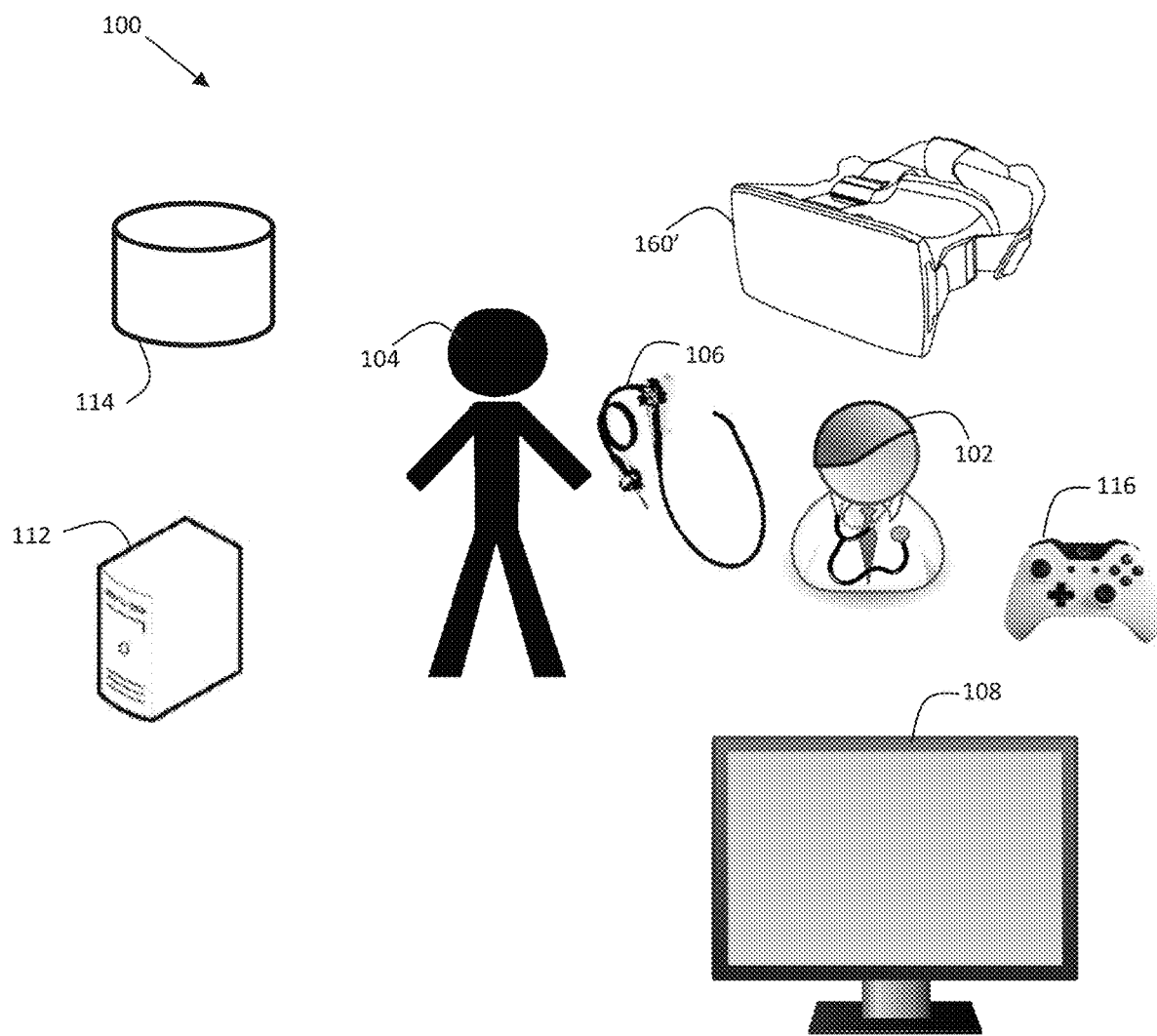
FIG. 1 illustrates an example Augmented Reality Surgical Navigation System.

The following acronyms and definitions will aid in understanding the detailed description:

AR—Augmented Reality—A live view of a physical, real-world environment whose elements have been enhanced by computer generated sensory elements such as sound, video, or graphics.

VR—Virtual Reality—A 3Dimensional computer generated environment which can be explored and interacted with by a person in varying degrees.

HMD—Head Mounted Display (FIG. 26) refers to a headset which can be used in AR or VR environments. It may be wired or wireless. It may also include one or more add-ons such as headphones, microphone, HD camera, infrared camera, hand trackers, positional trackers etc.

Controller—A device which includes buttons and a direction controller. It may be wired or wireless. Examples of this device are Xbox gamepad, PlayStation gamepad, Oculus touch, etc.

HMD Switch—Switch which allows the user to interact with the software using the HMD and/or the Controller. This switch can be activated/disabled in several ways, including: Pressing a button in the software or the Controller; Saying a phrase or a word, for example—"Start HMD", "Stop HMD"; Pressing a foot switch; and Hand gesture such as a long wave.

Segmentation—The process of partitioning a digital image into multiple segments (sets of pixels). The goal of segmentation is to simplify and/or change the representation of an image into something that is more meaningful and easier to analyze.

Clipping—The process of removing layers (one pre-set thickness at a time) of modeled anatomy perpendicular to the angle of view in order to reveal internal structures "slice by slice". Layers are removed in the lateral/distal to the medial/proximal direction.

SNAP Case—A SNAP case refers to a 3D texture or 3D objects created using one or more scans of a patient (CT, MR, fMR, DTI, etc.) in DICOM file format. It also includes different presets of segmentation for filtering specific ranges and coloring others in the 3D texture. It may also include 3D objects placed in the scene including 3D shapes to mark specific points or anatomy of interest, 3D Labels, 3D Measurement markers, 3D Arrows for guidance, and 3D surgical tools. Surgical tools and devices have been modeled for education and patient specific rehearsal, particularly for appropriately sizing aneurysm clips.

Scene—Refers to the 3D virtual space, which includes the 3D texture and the 3D objects in it.

Add On Sensors—Devices that allows receiving more information from the real environment in order to enhance the virtual experience. For example—Microsoft Kinect, Leap Motion.

Avatar—The point of view of the user is designated with a "skull shadow" (FIG. 1-101), referred to as "Avatar". The Avatar of the user follows the head movement of the surgeon and, for example, if the surgeon's head moves to the right, the Avatar will move to the right, etc. in all directions. If the surgeon desires another point of view, the Avatar can be repositioned to a new point inside the MD6DM using a controller.

MD6DM—Multi Dimension full spherical virtual reality, 6 Degrees of Freedom Model. It provides a graphical simulation environment which enables the physician to experience, plan, perform, and navigate the intervention in full spherical virtual reality environment.

The MD6DM provides a graphical simulation environment which enables the physician to experience, plan, perform, and navigate the intervention in full spherical virtual reality environment. In particular, the MD6DM gives the surgeon the capability to navigate using a unique multidimensional model, built from traditional 2 dimensional patient medical scans, that gives spherical virtual reality 6 degrees of freedom (i.e. linear; x, y, z, and angular, yaw, pitch, roll) in the entire volumetric spherical virtual reality model.

The MD6DM is built from the patient's own data set of medical images including CT, MRI, DTI etc., and is patient specific. A representative brain model, such as Atlas data, can be integrated to create a partially patient specific model if the surgeon so desires. The model gives a 360° spherical view from any point on the MD6DM. Using the MD6DM, the viewer is positioned virtually inside the anatomy and can look and observe both anatomical and pathological structures as if he were standing inside the patient's body. The viewer can look up, down, over the shoulders etc., and will see native structures in relation to each other, exactly as they are found in the patient. Spatial relationships between internal structures are preserved, and can be appreciated using the MD6DM.

The algorithm of the MD6DM takes the medical image information and builds it into a spherical model, a complete continuous real time model that can be viewed from any angle while "flying" inside the anatomical structure. In particular, after the CT, MRI, etc. takes a real organism and deconstructs it into hundreds of thin slices built from thousands of points, the MD6DM reverts it to a 3D model by representing a 360° view of each of those points from both the inside and outside.

The disclosed system is implemented on a modeling system such as the example surgical graphical tool (SNAP) which integrates with operating room technology to provide advanced 3D capabilities and augmented reality, allowing surgeons to enhance their surgery performance and prepare in advance. The SNAP tool provides neurosurgeons with unique virtual-reality guidance to determine the safest and most efficient pathway to remove cerebral tumors and treat vascular anomalies, for example, among other uses.

The SNAP tool imports the 3D planning of craniotomy, head position, path approaches to the pathology, for example for Keyhole and other minimally invasive techniques. The SNAP allow the surgeon to see in advance the expected surgeon eye view.

With the SNAP tool, surgeons can execute their surgery plan while in the operating room utilizing a particular patient's actual CT/MRI (and other) scans, allowing enhanced accuracy and efficiency. SNAP also provides innovative features that allow surgeons to see behind arteries and other critical structures, in a rotatable 3D format that can be modified to make the images more useful to the surgeon. For example, SNAP provides the ability to rotate images or make the semi-transparent, to aid the surgeon in visualizing the operation. SNAP makes use of advanced imaging technology that allows a surgeon to perform a real-life "fly through" of a "patient-specific" surgery. The tool provides preparation support outside the operating room and can also be utilized to take the pre-planned pathway into the operating room itself to be used by the surgeon (and his staff) during a procedure.

The SNAP obtains the tracing coordinates of surgery tools, navigation probe, microscope focal point etc. by either connecting to OR intra-operative tracing navigation systems. The SNAP provides 3D navigation model that slows enhanced situational awareness. SNAP can receive image or tracking/navigation information from any of these surgery tools that are configured to collect such information, and such information can be used by the SNAP system to cause the high-resolution image displayed to the surgeon to correspond to the received information. For example, the SNAP image might track the location of the tool in the displayed image, or update the image based on visual information provided by the tool, for example.

SNAP proximity warning systems operates in a similar way that Ground Proximity Warning System (GPWS) and An Airborne Collision Avoidance System (ACAS), Terrain Collision Avoidance System (TCAS) and other similar systems in airplanes which indicate and warns the air crew from proximity and/maneuver that may cause a proximity to the ground and other obstacles. SNAP proximity warning systems operates includes the following main stages:

The SNAP proximity warning systems can automatically mark anatomical structure that the surgeons need to avoid. Such anatomical structure may include fiber track, nerves, vessels, arteries etc.—The SNAP proximity warning systems allows a manual placement of Markets within the 3D or 2D navigation scene. Those Markets can either mark obstacles and anatomical structure to avoid or mark a Target that surgeon will navigate to. Every Marker that is being placed can be labeled, have a specific color, specific shape etc.—The indication of the warning of the SNAP proximity warning systems can be visual (for example changes in color), vocal (sound) and others.

The SNAP can allow creating a Trajectory. By marketing Entry point and then associating this entry point with the above Marker/target, the SNAP creates a Trajectory that allows to navigate from the Entry point to the Target.—The SNAP Path planner allows surgeons to connect several, Markers, Target and Entry points and do create Path. Multiple Paths can be created. Path can be a desired route to follow or a Path to avoid.

The SNAP provides visual graphic guidance to the surgeon. As far as the surgeon maintains his movements within the guided markers, the he will get accurately from point A to point B (from Entry point to Target). The tool provides institutions (e.g., hospitals) and their respective surgeons with the opportunity to reduce surgical errors, decrease the amount of surgical waste and related costs, reduce operating room time, and minimize the high-risk nature of the procedures. The tool provides for an opportunity to maintain high quality in neurosurgery training, and for taking the Education outside of the operating room: Halstedian training for surgery skills depends on a large volume, a wide variety of cases, and almost endless resident's time in the hospital. Recent developments have forced a rethinking of the Halstedian system. The recent constellation of pressures on Halstedian system includes; restricted work hours, increased public scrutiny, and reduction in operative experience.

Rehearsal using the tool can reduce the need for follow-up procedures and adjustments. For example, the tool, when used for aneurism surgery, using the tool can reduce the need for adjusting or replacing an aneurism clip. Adjustments and replacement of the clip can typically result in extended temporary occlusion and overall longer procedure time. This may increase overall procedure risk.

As will be appreciated by one of skill in the art, the example embodiments disclosed herein may be actualized as, or may generally utilize, a method, system, computer program product, or a combination of the foregoing. Accordingly, any of the embodiments may take the form of an entirely hardware embodiment, an entirely software embodiment (including firmware, resident software, microcode, etc.) for execution on hardware, or an embodiment combining software and hardware aspects that may generally be referred to herein as a "system." Furthermore, any of the embodiments may take the form of a computer program product on a computer-usable storage medium having computer-usable program code embodied in the medium.

Figure 31A:
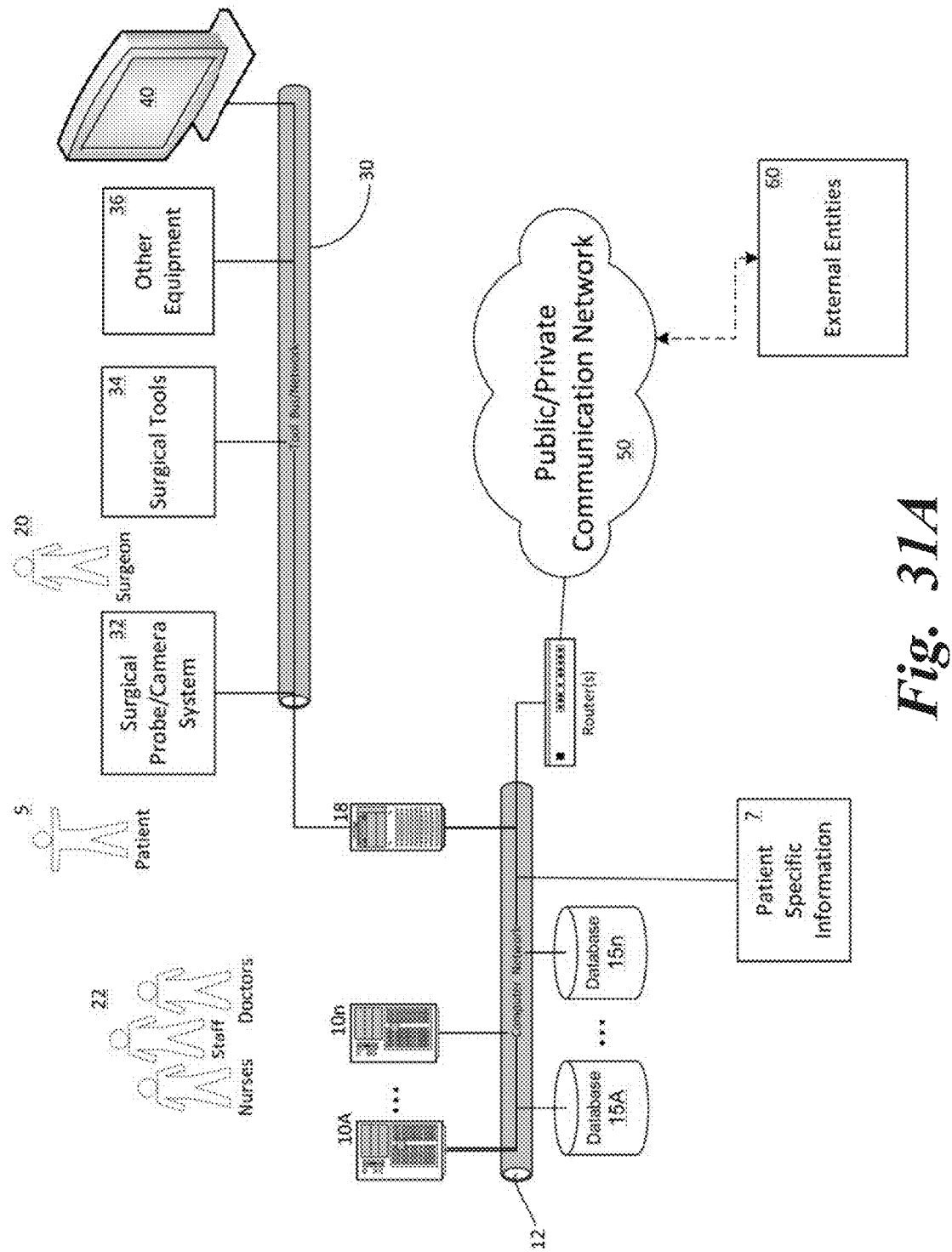
FIG. 31A is a block diagram showing an example system structure and interfaces for utilizing an example SNAP system that can be used with the improvements disclosed herein.

For example, the features disclosed herein can be implemented using a networked computer system 1 provided in a hospital setting (such as in an operating room), as shown in FIG. 31A. This system can be provided in the surgical setting, where a surgeon 20 operates on a patient 5 supported by various surgical staff 22. Such a system 1 integrates one or more servers (e.g., PCs) 10A-10n accessing data from one or more databases 15A-15n that are networked together using a computer network 12. The system will execute proprietary software provided to implement the functions and other features described herein. One or more computers 20 can be used to interface with various surgical tools such as a surgical probe/camera 32, other surgical tools 34, and/or other equipment 36 connected to the computer(s) 20 using one or more computer busses or networks 30 as an interface between the computer 18 and the tools. Note that in some situations, all of the computers 18, servers 10, and databases 15 might be housed in a single server platform.

The system is connected to a high-resolution 3D display 40 on which the surgeon can monitor the operation and activity of the various tools 32, 34, and 36. In some cases, a display may not have 3D capability. Furthermore, the Example Head Mounted Display (HMD) described below can be utilized to provide realistic images to the surgeon and/or his/her assistants. One or more such displays may be provided remotely from the operation location, such as through a connection via a communication network such as the Internet.

The system is configured with patient specific parameters 7 which include imaging details of the patient including images prepare from the patient's available CT and MRI images that were previously obtained, and other information that concerns the simulated models such as patient age, gender, and so on (some or all of which may be obtained from external entities, such as medical databases, laboratories, or other sources, for example). The system utilizes tissue information parameters obtained from a system database(s) that describe tissue and organ features. The system can be configured to interact with one or more external entities 60 via a communication network 50, such as the Internet, where desired.

Any suitable computer usable (computer readable) medium may be utilized for storing the software for execution on one or more of the computers for realizing the disclosed processes and for storing the disclosed data and information. The computer usable or computer readable medium may be, for example but not limited to, an electronic, magnetic, optical, electromagnetic, infrared, or semiconductor system, apparatus, device, or propagation medium. More specific examples (a non-exhaustive list) of the computer readable medium would include the following: an electrical connection having one or more wires; a tangible medium such as a portable computer diskette, a hard disk, a random access memory (RAM), a read-only memory (ROM), an erasable programmable read-only memory (EPROM or Flash memory), a compact disc read-only memory (CDROM), or other tangible optical or magnetic storage device; or transmission media such as those supporting the Internet or an intranet. Note that the computer usable or computer readable medium could even include another medium from which the program can be electronically captured, via, for instance, optical or magnetic scanning for example, then compiled, interpreted, or otherwise processed in a suitable manner, if necessary, and then stored in a computer memory of any acceptable type.

In the context of this document, a computer usable or computer readable medium may be any medium that can contain, store, communicate, propagate, or transport the program for use by, or in connection with, the instruction execution system, platform, apparatus, or device, which can include any suitable computer (or computer system) including one or more programmable or dedicated processor/controller(s). The computer usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, radio frequency (RF) or other means.

Computer program code for carrying out operations of the example embodiments may be written by conventional means using any computer language, including but not limited to, an interpreted or event driven language such as BASIC, Lisp, VBA, or VBScript, or a GUI embodiment such as visual basic, a compiled programming language such as FORTRAN, COBOL, or Pascal, an object oriented, scripted or unscripted programming language such as Java, JavaScript, Perl, Smalltalk, C++, Object Pascal, or the like, artificial intelligence languages such as Prolog, a real-time embedded language such as Ada, or even more direct or simplified programming using ladder logic, an Assembler language, or directly programming using an appropriate machine language.

The computer program instructions may be stored or otherwise loaded in a computer-readable memory that can direct a computing device or system (such as described by example system 1 of FIG. 31A), or other programmable data processing apparatus, to function in a particular manner, such that the instructions stored in the computer readable memory produce an article of manufacture including instruction means which implement the functions/acts specified herein.

The software comprises specialized computer program instructions that are executed by being provided to an executing device or component, which can include a processor of a general purpose computer, a special purpose computer or controller, or other programmable data processing apparatus or component, customized ad described herein such that the instructions of the specialized computer program, when executed, create means for implementing the functions/acts specified herein. Hence, the computer program instructions of the customized software are used to cause a series of operations to be performed on the executing device or component, or other programmable apparatus to produce a computer implemented process such that the instructions which execute on the computer or other programmable apparatus the steps for implementing the functions/acts specified in this disclosure. These steps or acts may be combined with operator or human implemented steps or acts and steps or acts provided by other components or apparatuses in order to carry out any number of example embodiments of the invention. The customized software may also utilized various commercially available software such as computer operating systems, database platforms (e.g. MySQL), or other COTS software, as desired.

For an example system, called the "Surgical Navigation Advanced Platform" (SNAP), medical images of an actual patient are transformed into a dynamic, interactive 3D scene. This dynamic and interactive image/model creates a new novel and original standard for medical imagery and has many applications.

The SNAP provides surgeons (neurosurgeons etc.), doctors, and their aids a unique virtual-reality guidance to determine the safest and most efficient pathway to remove tumors (cerebral etc.) and treat anomalies as vascular anomalies for example. The "Surgical Navigation Advanced Platform" (SNAP) can be used as a stand-alone system or an application of surgery navigation systems or used with a 3rd party navigation system for the type of procedures for which the 3rd party navigation system is used. These Procedures include but are not limited to Cerebral, Spine, and Ear, Nose Throat (ENT).

The SNAP allows surgeons to analyze and plan a specific patient's case before surgery, and then take that plan into the operating room (OR) and use it in conjunction with the navigation system during surgery. The SNAP then presents the navigation data into the advanced inter-active, high quality 3D image, with multiple points of view.

The SNAP is actually image guided surgery systems including a medical imaging device that present real time and dynamic multiple line of sights views (from different/multiple perspectives) of the surgery procedure. The image includes the scanned medical image (based on scan such as CT, MM, Ultrasound, X-ray etc.) and the surgery instruments. It may also include real time video and models based on video form microscope or other sources. The SNAP provides a real time 3D interactive guided image for the surgeon. The orientation of the anatomical structures (i.e. head, brain, knee, shoulder etc.) is market and pre-registered both in the physical/patient's and the scanned medical image (CT, MRI, Ultrasound, X-ray etc.); therefore, the orientation of the scanned medical image and the real anatomical structures of the patient's under the surgery are synchronized and aligned.

Furthermore, the above pre-registered markers provides a spherical reference for tracking the surgery instruments and the OR microscope (and/or the surgeon head) and therefore allowing to present the surgery instruments image/model in space in relation to the scanned medical image.

The patient's anatomical structures in 2D or 3D and the position and orientation of the surgery instruments are synchronized in real time and are presented to the surgeon with a real time location and orientation of the instruments and markers in space in relation to the anatomical structures.

The SNAP system is capable of preparing cases that have multiple scanned datasets. The built-in "Fusion" mode allows the user to select one dataset to serve as the primary dataset, and add secondary datasets, that will be aligned ("Fused") to the primary scan dataset.

The SNAP system has a unique clip features. The ANY plane IG cube clipping is a feature that the user can "clip" the 3D model from any desired angle, essentially cutting into the model and removing a section to expose the internals of the model. The clipping plane is the plane by which the 3D model is "Clipped" the plane defined by 2 variables—Plane normal (vector) and plane position (The point in space that the plane goes through).

Furthermore, the SNAP system knows to slave the ANY plane IG cube clipping to 3D moving elements in the scene. Since the cube-clipping plane is defined by a normal and a position, we can use moving elements in the scene to define this for the user. The elements are: The navigation probe, the 3D controller (Omni), the corridor, the IG point of view (Eye camera) etc.

Another feature is the Transfer Function. The SNAP system has a special ability to display "Tissue specific intensity". The original dataset slices are collected and stacked to reconstruct a cube of pixels, or what we call the voxels cube. The 3D model is a cube volume of voxels. The transfer function is used to map each voxel intensity value to color and opacity. That way we control the tissue intensity and enabling a surgeon to see what he typically can't see. This innovative feature allows surgeons to see behind arteries and other critical structures, something not possible until now.

The SNAP can present models on one or multiply windows on the same screen or on multiply screens. Examples for the features and applications of the SNAP, multiple features can be activated side by side on the screen.

Figure 31B:
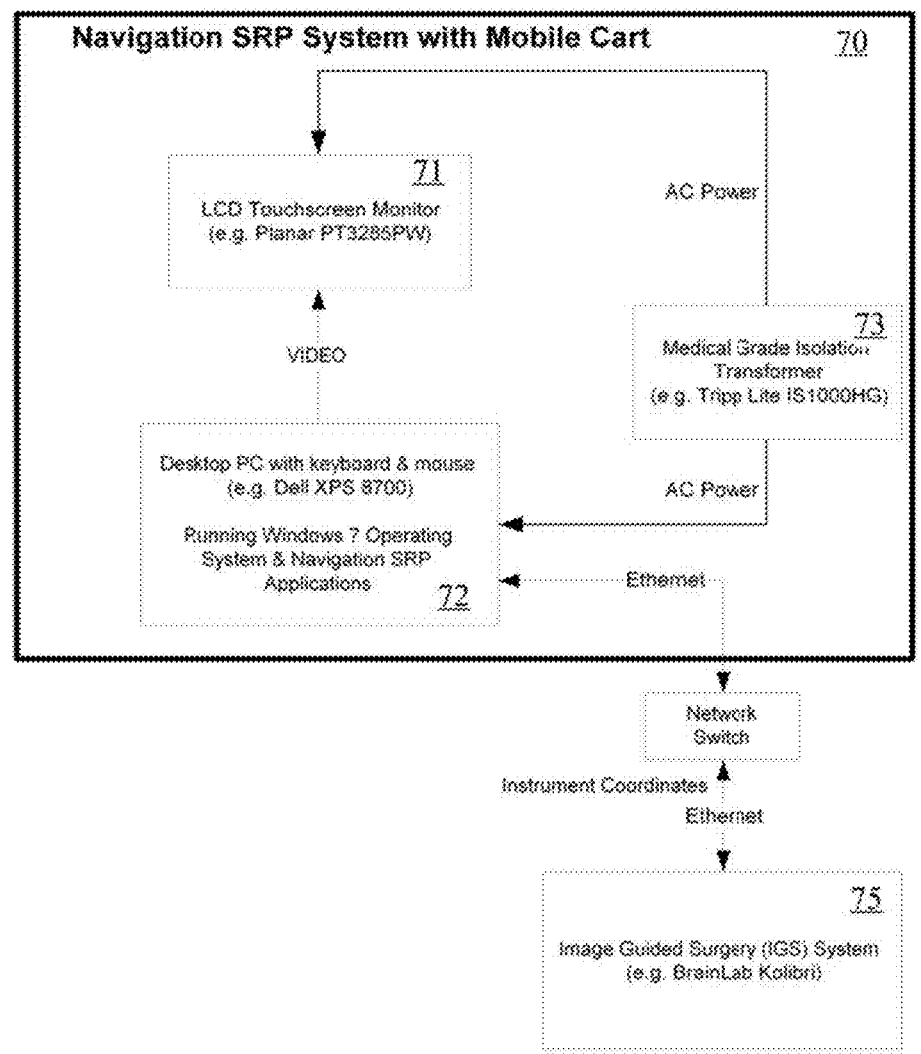
FIG. 31B is a block diagram showing example SNAP tool components for the example SNAP system.

A typical SNAP system configuration is comprised of the following main components: (1) System mounted cart for mobility; (2) Medical grade isolation transformer; (3) a Personal Computer (or server) running Microsoft Windows 7 operating system; (4) a high end nVIDIA graphics adapter for high quality graphics; (5) a 27" or 32" full HD touch screen display; (6) a medical grade keyboard and mouse; and (7) a SNAP Software Application for implementing the features described herein. Such a system is shown by the block diagram of FIG. 31B, where an example mobile cart mounted SNAP system 70 comprising a touchscreen monitor 71 is configured with a PC 72 and a power system 73, all of which can be provided in the operating room. The example system 70 is connected to a navigation system 75 provided in the operating room, such as the example Image Guided Surgery (IGS) System, from which the SNAP system 70 can receive data so that the SNAP system 70 can display high resolution, realistic 3D images that follow the operation of the navigation system, effectively enhancing the operation and display capabilities of the navigation system with the SNAP high-resolution imaging capability based on the images of the specific patient being operated on.

The Surgical Navigation Advanced Platform (SNAP) is intended for use as a software interface and image segmentation system for the transfer of imaging information from CT or MR medical scanner to an output file. A tissue segmentation window is provided to edit and update tissues segmentation to prepare a case. The change in tissue segmentation is reflected in the 3D image, and the result can be saved as part of the case file. It is also intended as both pre and intra-operative software for simulating/evaluating surgical treatment options. The Surgical Navigation Advanced Platform (SNAP) is a pre and intra-operative tool to simulate/evaluate surgical treatment options.

The system will typically provide EMC immunity that can be adapted for an operating room, and will utilize touchscreen operation for navigation, typing, and image manipulation. The system can store individual patient cases using a case file, which can be loaded into the system as desired. A surgeon can create a case from scratch, using scanned information (e.g., MR, or CT DIACOM image data files) and patient data of a particular patient. These cases can be edited and updated as desired. Editing windows can be used to edit and manipulate the images and files.

Generic models of various organs and tissues can be provided, which can be overlaid with patient specific models based on patient imaging or other diagnostic tools or laboratory inputs. Hence, for organs or other features not of particular interest, the system can use generic models (e.g., eyes or other organs) where patient specific information is not needed for the intended treatment.

The Surgery Navigation Advanced Platform (SNAP) displays patient specific dynamic and interactive 3D models with real time navigation data. When performing a navigation session, the tool can be used to verify the accuracy of the SNAP navigation pointer location (provided on the SNAP high resolution display) by pointing and touching visible structures on the patient (i.e. tip of nose, ear lobes) and verifying that the pointer on the SNAP screen points to the same location in the 3D model.

Figure 31C:
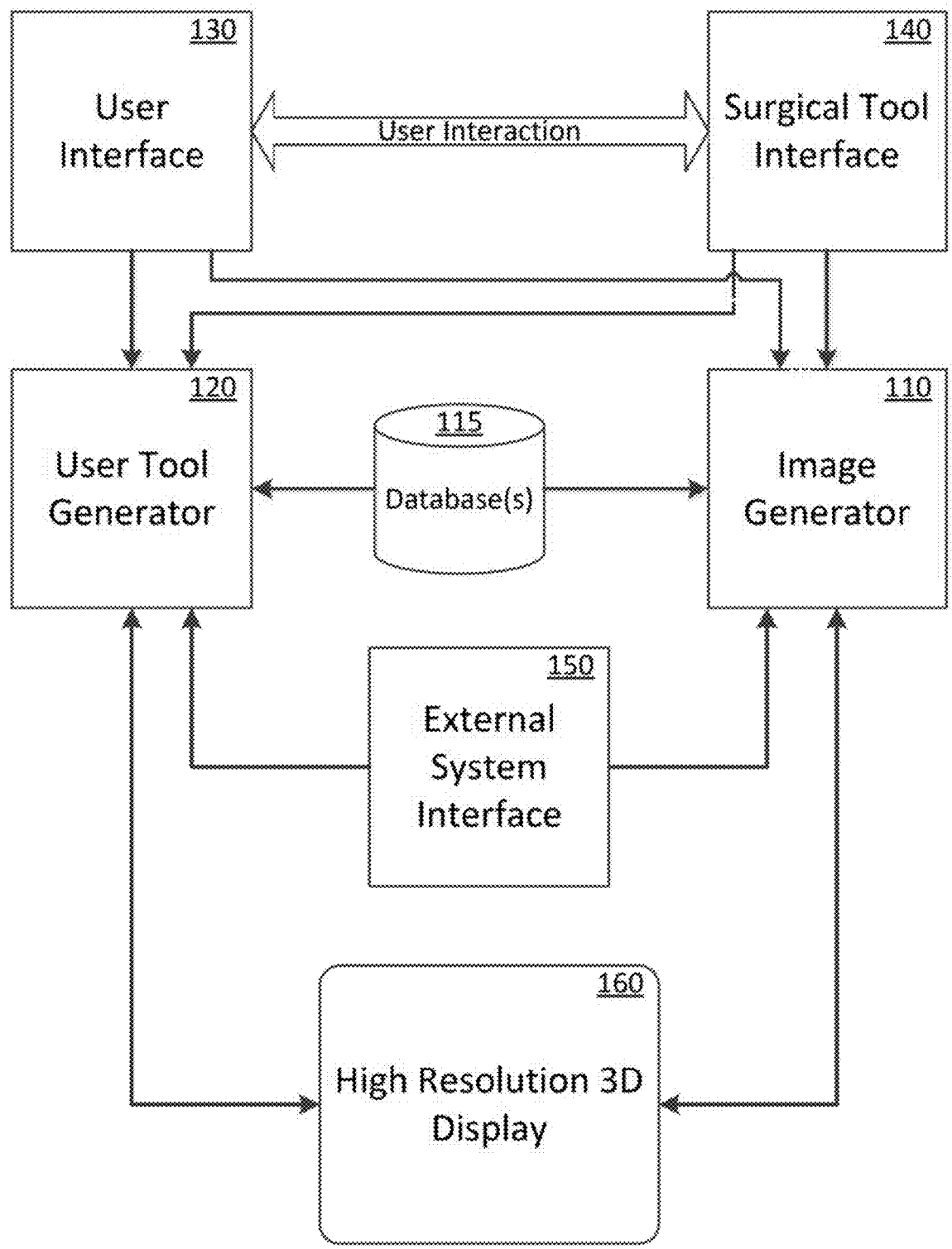
FIG. 31C is a block diagram showing example software interfaces for the example SNAP system.

FIG. 31C shows an example of the primary processing routines, driven by software modules, which generate the images provided by the SNAP tool. The Image Generator 110 generates the realistic tissue images for display on the display 160, using information stored on the database 115, such as generic tissue images, patient specific images, and the like. The image generator 110 assigns visual representation of each segment (shadow texture and so on) and the mechanical Properties and other modeling features will provide the realistic images.

Similarly, the user tool generator will generate realistic images of surgical tools that are displayed dynamically interacting with the tissue images generated by the image generator. In a surgical environment, the tool images displayed on the display 160 may represent actual surgical tool interfaces 140, representations of which could be generated for display by the image generator 110 or the user tool generator 120, for example. The surgical tool interface may dynamically interact with the tissue images generated by the image generator 110. Again, specifications and details about the tool images may be stored in the database 115. Note that because the display 160 may be a touchscreen display, the display 160 may act as the user interface 130, along with other devices such as a keyboard, mouse, or other input device. Also, the display 160 may include a Head Mounted Display as part of the display 160 to provide the surgeon and/or other participants a realistic visual image.

The SNAP tool also provides an external system interface 150 that allows the system to interface to other external systems that provide navigation or other functions to the surgeon, so that the SNAP tool can generate images that are consistent with the outputs of the external systems, e.g., mirror the navigation or update the imaging based on the operation of the external system(s). The SNAP tool can then update its display images appropriately for providing an integrated view to the surgeon in high resolution, 3D images that interact with the graphical tools.

Once the surgery tools and the other objects are selected by the surgeon, they are integrated into the virtual surgery scene displayed by the display 160 and turn into an integrated element of the simulated scenario including realistic visual features and mechanical properties and operation properties features that are applied to each one of those selected items, for example—displayed scissors have the real mechanical characteristics and will cut as the real scissors do, and, Aneurysm clips, when placed at the vessel, blocks the blood flow. In this manner, the displayed tools interact with the tissue models in a realistic manner, but in a way that surgeons can manipulate to provide viewpoints not possible in the real world, such as by making various features transparent, rotating images, reversing a procedure, etc.

The interactive image/scene that is displayed to the surgeon is constructed from elements that are both volumetric rendered elements and surface rendered elements. Furthermore, each element, volume or surface, interacts with one or more elements that are volume. Interaction between elements includes, but is not limited to, physical interaction such as: a collision model implemented to represent the interaction between elements that results with movements and/or reshape of elements that replicate the actual physical movements of the element according to physical conditions, such as pressure, elements material (elasticity, stickiness etc.), and collision condition such as collision angels and elements orientation.

The rendering process equation can account for all lighting shadow and shadowing phenomena and produce a final output stream that incorporates all the visual elements.

Anatomical structures that were created using a Tissue Paint or a Magic Tissue Wand algorithm and integrated with the scanned images are an integrated part of the image. For example, a vessel that anatomical structures that originally was partial and complete, after applying the Magic Tissue Paint and Tissue Wand algorithm will become a complete anatomical structures with structure that is combined from the original scanned image and the new created structure. Furthermore, a control (check box) allows to select the new created structure and to switch between on (showing the new created structure) or off (hiding the new created structure). Additionally, an option is provided for selection to render the new created structure in a volume and or mash/polygon rendering/reconstruction.

A developed algorithm and software tool provides the user an interface to draw any geometric shape or free hand drawing shape in 2- or 3-dimensions (e.g., line, circle, clinic, ball etc.). The region that is included/enclosed/captured within the said geometric shape (2- or 3-dimensions) is defined as a "Marked Region". The user then, has the ability to define and assign any visual characteristics and any mechanical properties to that "marked region" including the ability to paint portions of images, make them transparent or shade them, for example. Virtual light sources can be provided with characteristics that include: spherical location in space, color of the light, strength of the light, the aspect ratio, the geometric shape of the virtual source etc.

Structures that are created r with the Tissue Paint, Magic Tissue Wand algorithm or the Marked Region can be assigned with desired mechanical properties characteristics. The mechanical properties coefficients of any anatomical structure (stiffness, elasticity etc.) can be tuned by the user to create a tailored made mechanical behavior.

The system provides Real Time Tracking and Feedback to track a real surgery instrument during the surgery. The tracking system transfers the surgery instruments location and coordination in space relative to the orientation and location of a real anatomical structure (for example, specific spot on the patient's head). The instruments' location and orientation is then sent to the surgical simulating system. Feedback is provided to the surgeon based on the patient specific simulation and the instruments' location and orientation. One example for such feedback can be; the system generates feedback to the surgeons for the type of tissue he is dissecting and alarming the surgeon in case that he dissects healthy brain tissue instead of a tumor. Additional example is that after that the surgeon applied an implement on the real anatomical structure (for example an aneurysm clip applied on an aneurysm on the real patient), the system allows the surgeon to rotate the simulated image/model that is princely oriented as the real anatomical structure based on the tracking, and observe and evaluate the location and efficacy of the placed implant.

This tracking and feedback of the real instrument can be accomplished in a number of ways, such as by using a video system to track the location and movement of the instrument and the patient features. Alternatively (or in addition to video tracking) the surgical instrument may be modified to enable tracking, such as by using GPS, accelerometers, magnetic detection, or other location and motion detecting devices and methods. Such modified instruments may communicate with the SNAP tool using WiFi, Bluetooth, MICS, wired USB, RF communication, or other communications methods, for example (e.g., via surgical tool interface 140 in FIG. 31C).

Leveraging the scanned views, or traditional DICOM images, the system 100 renders a complete, continuous, real time spherical model that can be viewed from any angle, perspective, or orientation, while "walking" or "flying" inside the anatomy using a VR, AR, mixed reality, merged reality, or marriage reality headset 110. In other words, the system 100 enables a surgeon/user 102 to "tour" the inside of the anatomy. It should be appreciated that "walking," "flying," and "touring" indicates the surgeon 102 freely and virtually navigating and exploring inside an anatomy in order to gain perspective on the various anatomical structures as if the surgeon 102 was actually physically inside the anatomy.

Thus, when wearing the VR headset 110, anatomical structures surround the surgeon 102 and the surgeon 102 can stand between a basal artery and the posterior side of a meningioma, for example. By moving his/her head to the left, the surgeon 102 may see the artery and by moving his/her head to the right, the surgeon 102 may see the tumor. The surgeon 102 may also look down toward the feet to see the spinal canal from above. In other words, the view is adjusted based on both the direction that the surgeon 102 is looking as well as the angle of view.

It should be appreciated that the experience that the surgeon 102 gains is an immersive 360 spherical experience. Thus, it's as if he is walking inside a room and can stand in between a couch and a shelf, for example, and turn his body to see the door, or walk over and stand between a wall and the cabinet. Similarly, in the context of a human anatomy, the surgeon 102 physically walks between a vessel on his left and a tumor on his right, for example. In addition, the surgeon 102 can walk around the tumor to tour all of the surrounding structures between the tumor, nerves, vessels, etc. By moving his head, the surgeon 102 is physically viewing the distance between one structure and another, and therefore he can get a real feel of the orientation of the structures and the intra-spherical relations between the structures. Thus, the surgeon is able to achieve a real sense of looking at the actual structure instead of just looking at pictures of the structure.

It should further be appreciated that the 360 model that is being walked through is built from a combination of: 1) scans (such as CT, MM, and similar); 2) post processed models such as DTI; and 3) blood flow analysis. These are all aligned and infused to create comprehensive view of the patient's 104 anatomy. The 360 model may also include optical information such as operating microscope visual, endoscopic visual, robotic arm visual, etc. This optical information may also be aligned with and synchronized with the 360 model.

It should be appreciated that the optic video may be traditional camera, a stereo camera, or a 360 camera, each of which can be fully infused within the 360 model.

In some examples, the 360 model can include additionally infused elements, such as manually added elements, for example, a trajectory path that the surgeon draws to assist in the surgery may be incorporated into the 360 model. Another example is models of the surgeon(s) 102 avatar(s) to represent the presence of the surgeon(s) 102 inside the anatomy may also be incorporated into the 360 model.

In one example, the 360 model may include generic anatomical models, for enhanced representation of the anatomical model. The generic models may be automatically incorporated or added manually. A source for the generic models may be a generic atlas of anatomical structures placed inside the 360 model.

In one example, a 360 model may also include drawings, models, or other relevant information incorporated from literature, articles, text, or other relevant sources that explain and elaborate on a specific pathology or educate the user about a specific pathological case.

In one example, the 360 model may include 360 markers. The markers can be placed anywhere in the 360 model to mark specific places in the 360 model. The markers can be labeled with text or other information. In one example, the markers include artificial intelligence capabilities and functions. For example, when the surgeon 102 walks within proximity of the marker, the marker can change colors, activate an audible alarm or notification, show additional information, or perform other suitable functions.

Moreover, beyond moving the head looking in different directions to observe various structures from a single point inside the anatomy, the system 100 further provides the surgeon 102 with the ability to change location inside the anatomy from which a perspective is being viewed. For example, a surgeon 102 can tour multiple fused data sets such as post processed DTI fused with vascular data from a CTA. The surgeon 102 can then walk into the space between a corticospinal tract and AVM nidus, for example. The surgeon 102 can further physically walk down a planned endoscopic or minimally invasive corridor, while standing at the tip of the virtual endoscope and see the path that the scope will maneuver during surgery.

It should be appreciated that the system 100 is capable of adjusting the view inside the patient's body in real-time as the surgeon's 102 perspective changes, based one or both simultaneous head position movement as well as movement inside patient's body in any of the three-dimensional X, Y and Z coordinates.

The SNAP system is enhanced and modified for using the MD6DM features to incorporate the augmented reality system described herein below. The MD6DM provides a graphical simulation environment which enables the physician to experience, plan, perform, and navigate the surgical intervention in full spherical virtual reality environment, with the addition of augmented reality features greatly expanding the functionality and usefulness of the SNAP system described above.

Figure 3:
FIG. 3 illustrates an example of an integrated view of the optic and scanned views on the same screen.

This modification results in an Augmented Reality Surgical Navigation System ("ARS") 100 described herein and illustrated in FIG. 1, which gives the surgeon 102 or another user (such as assistants, nurses, or other doctors) an integrated view of the optic and scanned views on the same screen (as illustrated in FIG. 3). Referring back to the system 100 of FIG. 1, the surgeon 102 can inspect specific patient 104 anatomy both in the pre-built model as well as live in the patient 104 simultaneously. The system 100 gives the ability to step into the MD6DM model and physically move the user's body and look around at specific structures. The user can look 360° around a targeted anatomy or pathology, and explore behind pathology to see how it is altering the patient anatomy. Thus, the surgeon 102 no longer needs to take his eyes off the microscope or endoscope 106 to look at patient scans, planning software or a MD6DM model because the virtual image and the real optical image are projected side by side, or fused together and displayed either on a display monitor 108 or on the Head-Mounted Display (HMD) 160'.

A computing device 112, such as the Surgical Theater "Endo SNAP" System (e.g., all or part of the SNAP system 1 as described above and shown in FIGS. 31A-31C modified to incorporate the features of MD6DM), enables the ARS system 100 by obtaining patient DICOM 2D images and building virtual models in real time or obtaining prebuilt models. Data is obtained from a database 114, for example. The ARS computing device 112 is further configured to integrate the prebuilt images with a live video feed received from the endoscope 106 based on navigation data also received from the tracking tip of the endoscope 106 to form an augmented reality view of the patient 104 with tracking capabilities. It should be appreciated that the multiple views (i.e. the live feed and the retrieved images) can also be viewed separately or in parallel either on the display monitor or through the HMD 160'.

Figure 2:
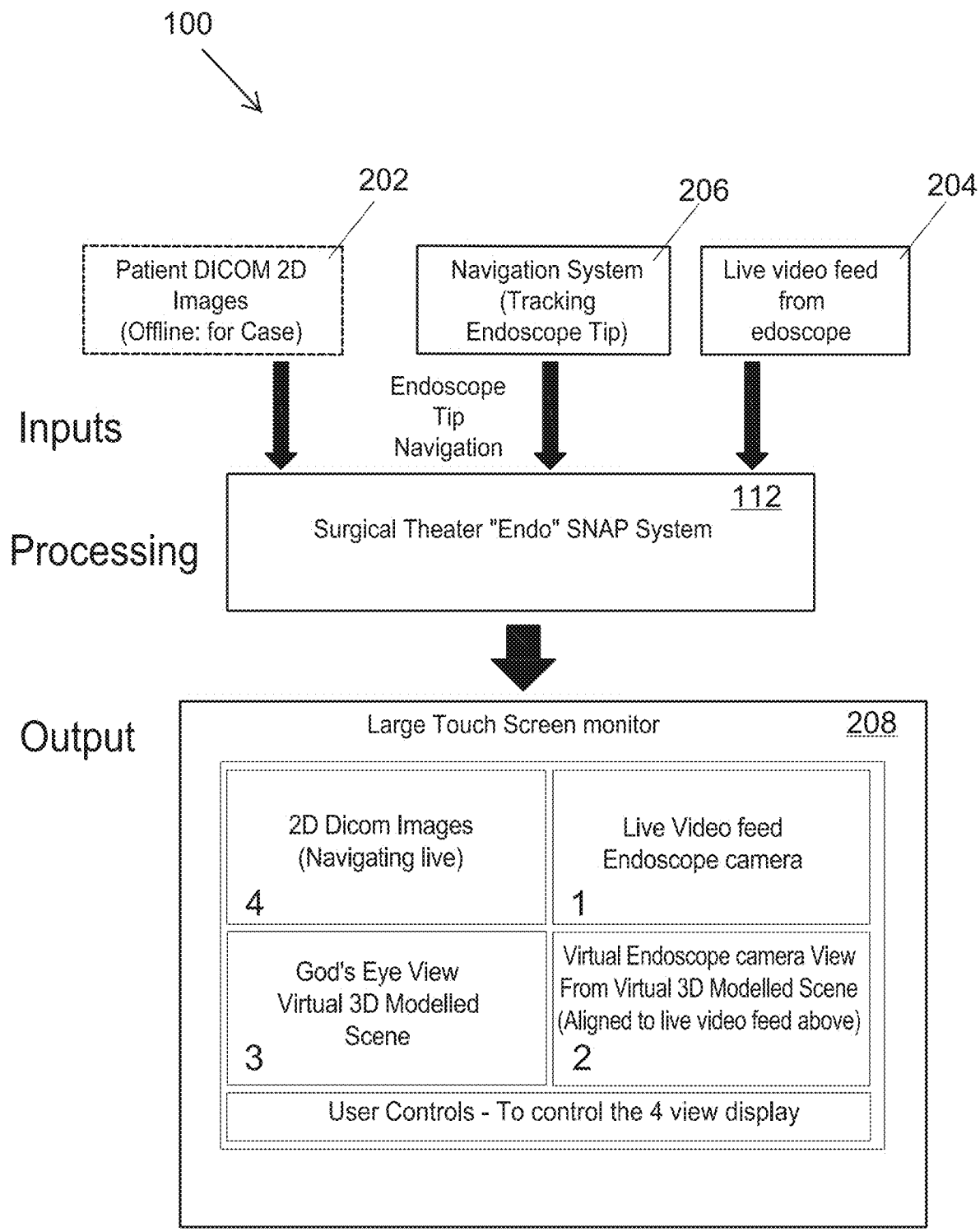
FIG. 2 illustrates a block diagram of an example Augmented Reality Surgical Navigation System.

FIG. 2 illustrates an example block diagram of the ARS system 100. The ARS computing device 112, such a Surgical Theater Endo Snap System, is configured to receive, as a first input, patient DICOM 2D images 202. The ARS computing device 112 is further configured to receive, as a second input, a live video feed 204, such as a video feed from an endoscope. The ARS computing device 112 is further configured to receive, as a third input, navigation system tracking data 206. In one example, the tracking data 206 is indicative of the position and orientation of a surgeon 102 relative to the patient 104. It should be appreciated that, based on such navigation system tracking data 206, the ARS computing device 112 is able to determine not only where in a room a surgeon 102 is positioned but also where the surgeon 102 is looking. For example, a surgeon 102 may be positioned on the right side of a patient 104 body. However, the surgeon 102 may view, from that position, a top of the patient's 104 head or a side of a patient's 104 head, for example.

With the appropriate navigation system tracking data 206, however, the ARS computing device 112 is able to calculate and pinpoint the angle of view in addition to location and therefore offer a more unique and distinct experience for the surgeon in the operating room. In particular, the ARS computing device 112 processes the three inputs 202, 204, and 206, and integrates them to form an augmented reality view of the patient 104 with tracking and navigating capabilities. The ARS computing device 112 is further configured to output the augmented reality view of the patient to a device 208 for viewing. The device 208 may be, for example, a display monitor 108 or a HMD 160' (or both). It should be appreciated that, although only three (3) inputs are illustrated, the ARS computing device 112 may be configured to receive any suitable number of inputs from a variety of suitable input sources in order to provide the surgeon 102 more complete information that may be helpful for performing a particular surgery. For example, the ARS computing device 112 may be configured to receive additional live video feeds or additional tracking and sensor information indicative of a surgeon's location within the operating room.

In one example, a HMD 160' may offer a surgeon 102 a direct actual pass-through view of a patient 104 without relying on a video feed. Thus, in one example, the ARS computing device 112 is configured to generate an augmented reality view without a live video feed. Instead, the ARS computing device 112 is configured to present a virtual model to the surgeon 102 via the HDM 160' such that the virtual model overlays the surgeon's 102 actual view of the patient 104 in order to provide the surgeon with an augmented reality view of the patient 104. The ARS computing device 112 relies on the navigation system tracking data 206 to synchronize the virtual model presented with the surgeon's 102 actual view of the patient 104.

It should be appreciated that the augmented reality view is continuously updated in real time as a surgeon's 102 position, orientation, or angle of view changes. Thus, as the surgeon 102 moves around the patient or adjusts his focus on a different position on the patient 104, the virtual model is adjusted so that the augmented reality view is synchronized with the such movements and stays true to the surgeon's 102 perspective.

Furthermore, the system can accommodate any number of additional users, such as additional surgeons, nurses, assistants, or others who may be present locally or located remotely and connected to the system via a communication network such as the Internet. The system can utilize information from any or all of these additional users to further augment the view using information from such additional users, such as the actions of a second surgeon supporting the medical procedure. In addition, the system can provided the augmented images as seen by the surgeon to any of these additional users, whether using an HMD display or some other type of display. Hence, is some embodiments, the action of assistants, such as nursed to assist the procedure could also be displayed as part of the augmented view, or as an additional augmented view.

An example of a process of working with the HMD 160' includes: 1) a user building a SNAP Case using a case wizard provided by the SNAP computing device 112, or selecting a pre-build SNAP Case from the database 114; 2) activating an HMD 160' Switch; and 3) depending on the type of HMD 160' and its configuration of Add On Sensors, the user can interact with the Scene and collaborate with others in a Virtual Collaboration Scene.

HMD 160' functionality is separated according to the functionality of the hardware, and in particular whether it is AR or VR, or both. If both hardware configurations are available, both modes will be available in the software. The user controls all of the system functionality using the Controller, Voice Commands, Hand Gestures, Virtual buttons, and other Add On Sensors. This allows the user to choose what is the most situationally appropriate or intuitive way for him to interact with the SNAP Case or to communicate with remote users while in Collaboration mode. All of the user interactions in the virtual world are also visualized on the SNAP display 108 monitor for external viewers to watch and understand what the user is seeing. The user is able to activate every functionality that is available on the SNAP system 112 while in one of the HMD modes. Available functionality in HMD modes include, but are not limited to, the ability to: change segmentation presets, select fusion layer, show/hide markers/path/trajectory, take slices in/out from the SNAP Case (Clipping), add virtual surgery tools etc. Activation or deactivation of those functionalities is done using the Controller, Voice Commands, Add On Sensors or virtual buttons in the Scene, for example.

Figure 32:
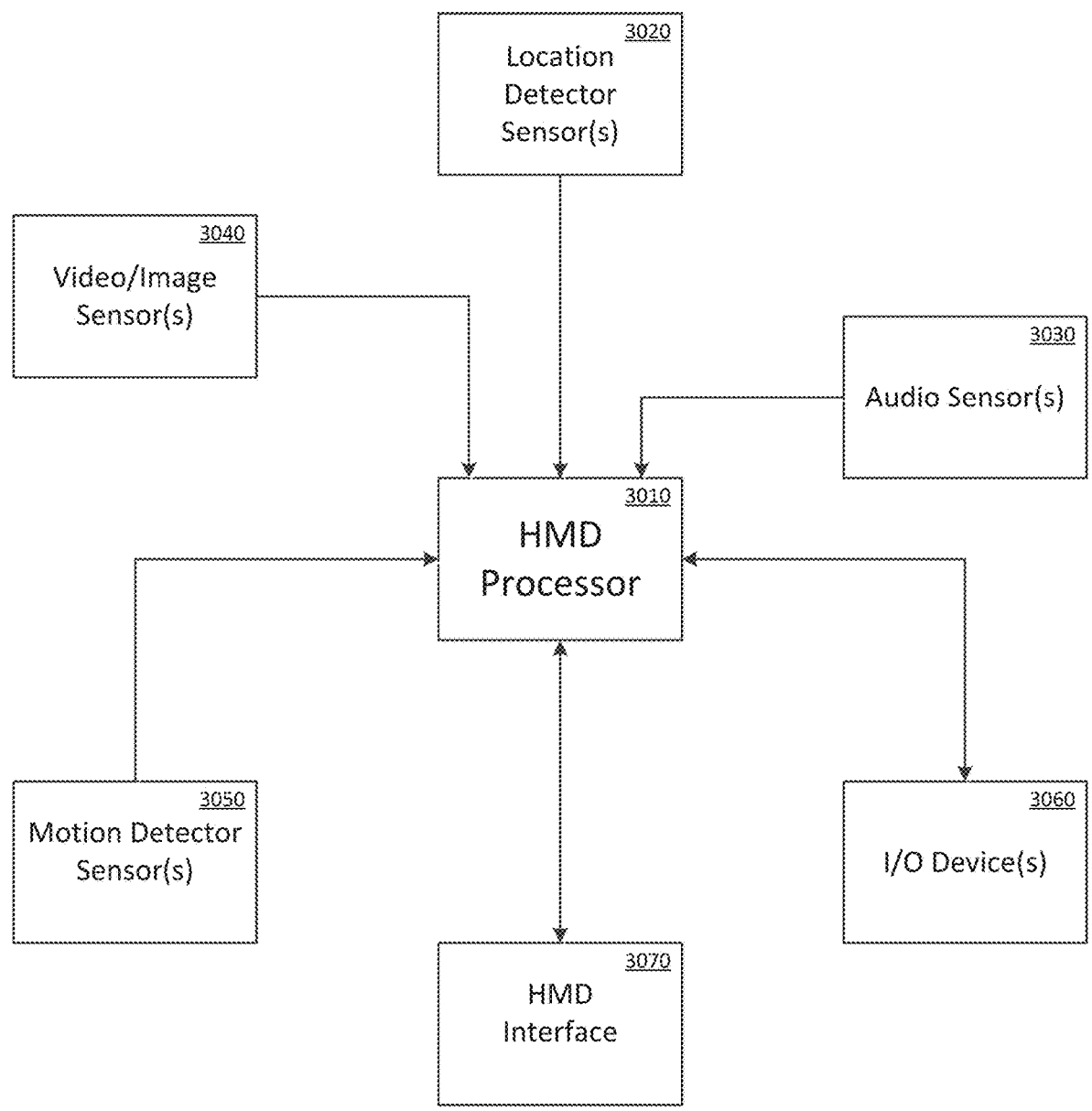
FIG. 32 is a block diagram showing various sensor components that can be utilized in any of the example head mounted displays.

FIG. 32 shows a block diagram with various sensors that can be provided with any of the disclosed HMD devices. Such sensors include one or more locations detector sensors 3020 (e.g., GPS), one or more video and/or image sensors 3040, one or more audio sensors 3030, one or more motion sensors 3050, and one or more Input/Output devices 3060 (such as a high resolution display, buttons, scroll devices, etc.). These sensors can communicate with an HMD processor 3010 which will interface with the SNAP system via an interface 3070. Other types of sensors and controls can also be provided.

Figure 29:
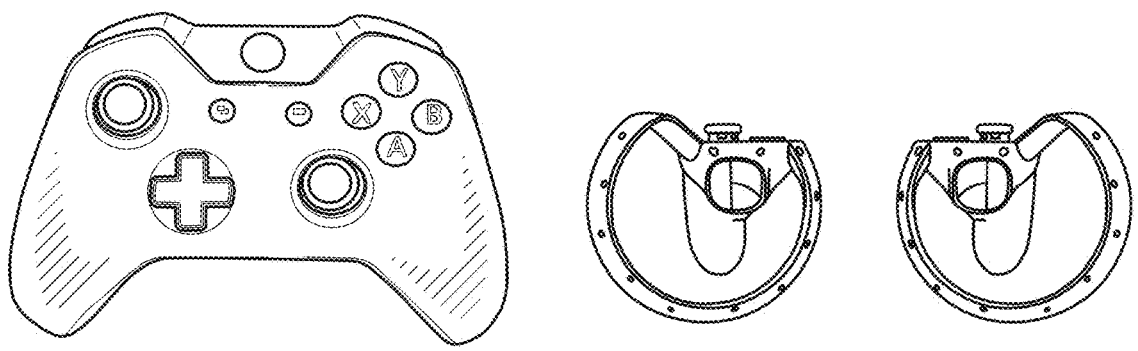
FIG. 29 illustrates example input controllers.

Example functionalities and controls include pressing a button on the Controller to filter out slices from the SNAP Case, making the hand gesture "swipe left" to rotate the SNAP Case left, saying keyword phrase "Show orientation" to take the user out of the SNAP Case view and give the user an overall look of his position, or pressing a virtual button in the Scene to select surgical tools for virtual use, among others. FIG. 29 shows example controllers that can be used as input devices to control these operations of the system.

In the VR mode, the user interacts with the SNAP Case in a purely virtual environment. The user can interact with the Scene in several ways including, for example:

Head movements—Using a rotational sensor of the HMD 160', the system tracks the user's head movements and angles and projects them into the Scene. This allows the user to change their view in the Scene in 360 degrees based on their movement and angle adjustments.

Controller—Using the direction controllers, the user can move in the desired direction based on where he is looking. Using other buttons, he is able to activate specific SNAP Core Functionalities or specific mode functionality. For example, pressing and holding a specific button on the controller gives the user an overall view of the Scene. This allows the user to understand his position and orientation in the scene.

Voice—Speaking keywords or phrases that are received by a sensor such as a microphone activates a specific functionality. For example, "Jump to marker 1" will move the user to the predefined marker 1 position. When Collaboration is available, "Move to Player 2 view" moves the primary user to the 2nd "Player's" position, and orients the primary user's view to the 2nd "Player's" orientation at that time.

Position sensor—Using a position tracking sensor to track the primary user's movements, the movements of the user will be translated to virtual movement in the Scene. Tracking user movement while in scene allows the user to select virtual buttons that will activate specific functionality.

Hand sensors—This allows the user to see a virtual representation of his hands and their position, and allows him to further interact with the SNAP Case in the Scene. For example, the user can interact with surgery tools, press virtual buttons, or rotate and pan the view using hand gestures.

Figure 4A:
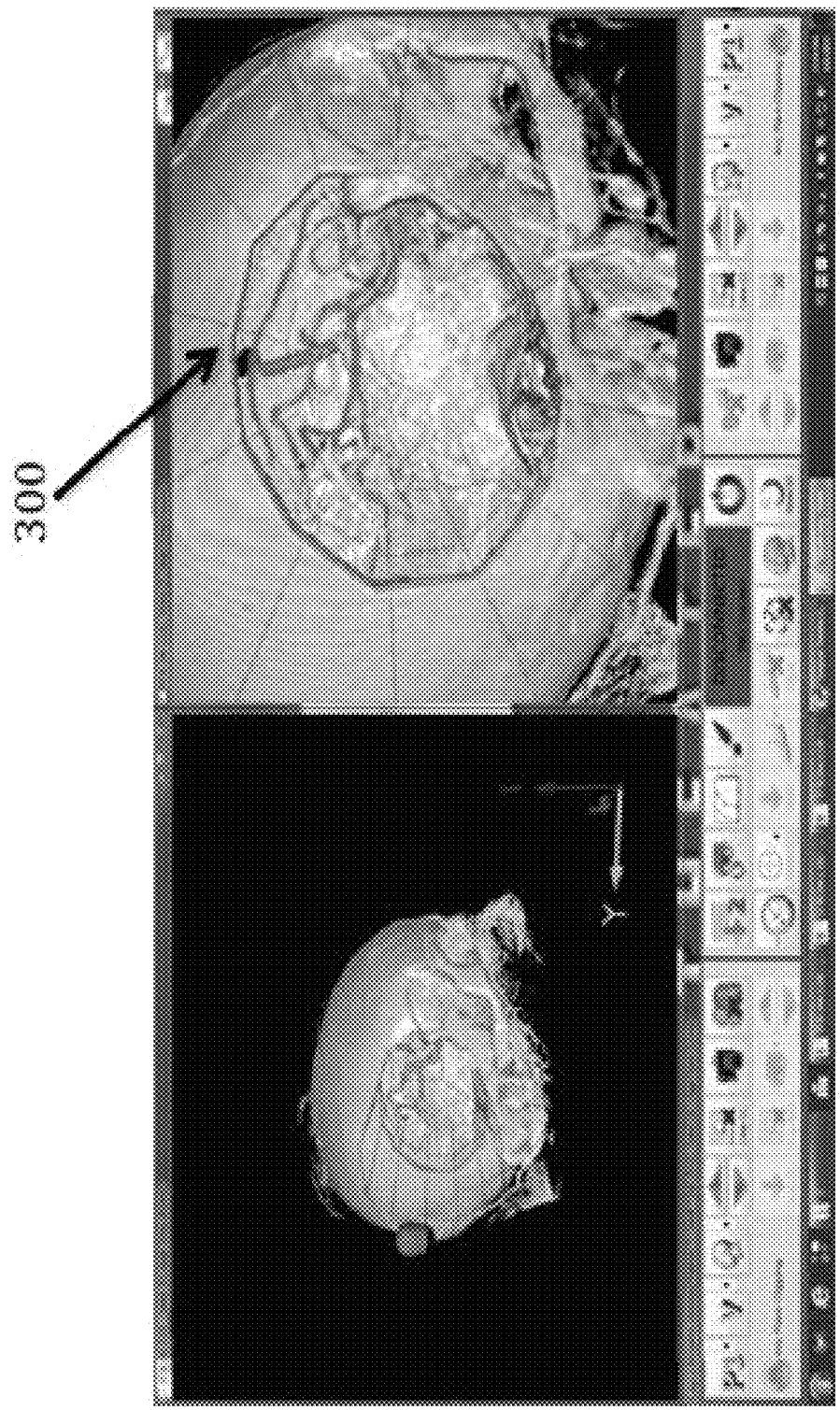
FIGS. 4A and 4B illustrate example views of a tumor case from outside the corridor.
Figure 4B:
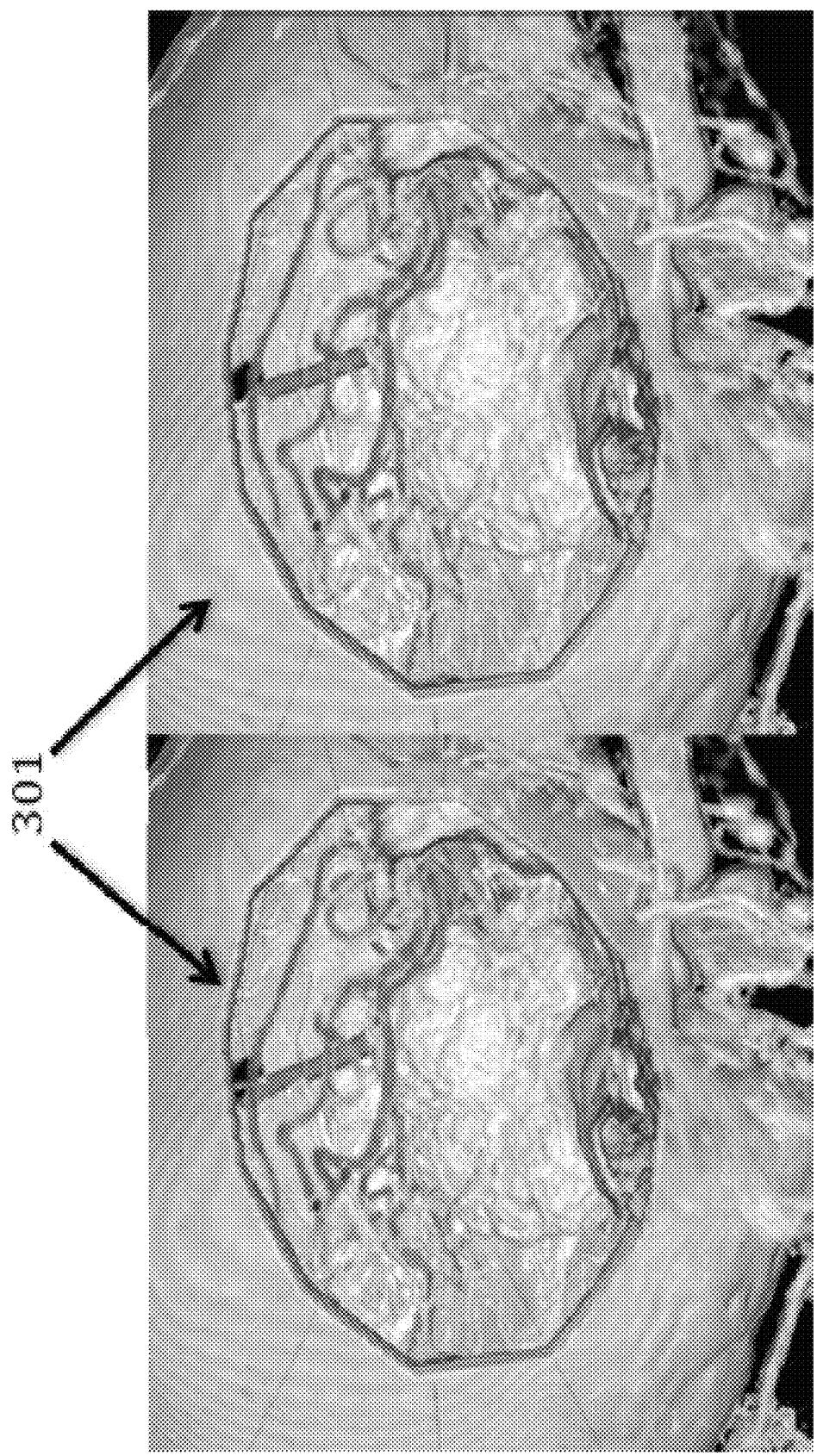
Figure 5:
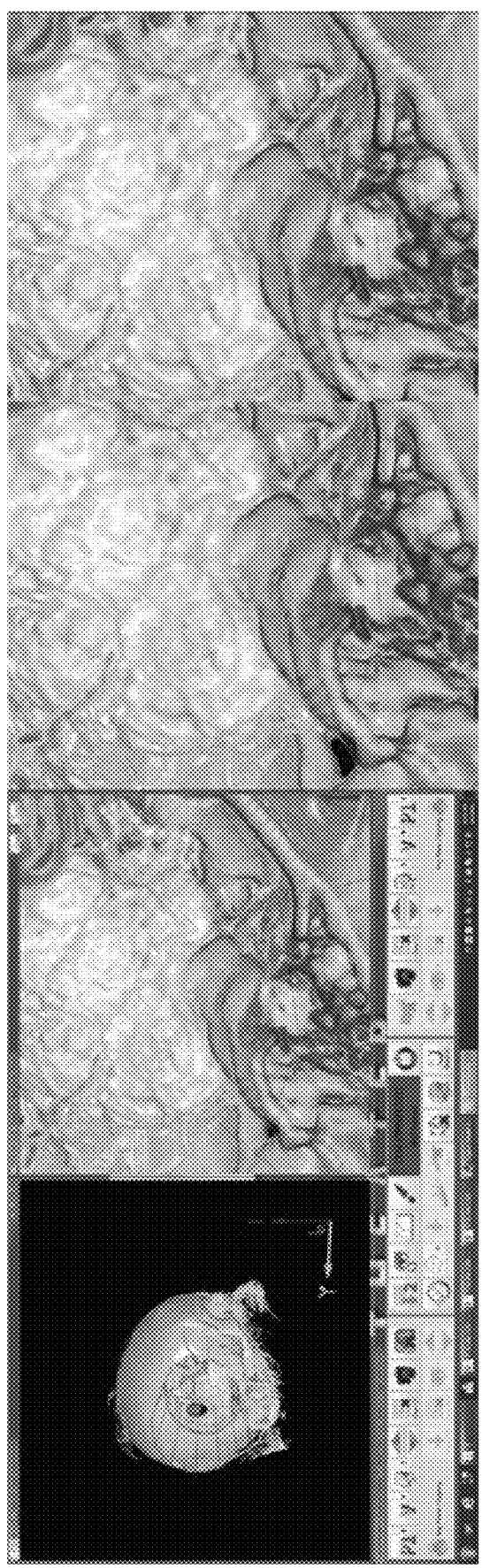
FIG. 5 illustrates an example view of a tumor case from inside the corridor.
Figure 6:
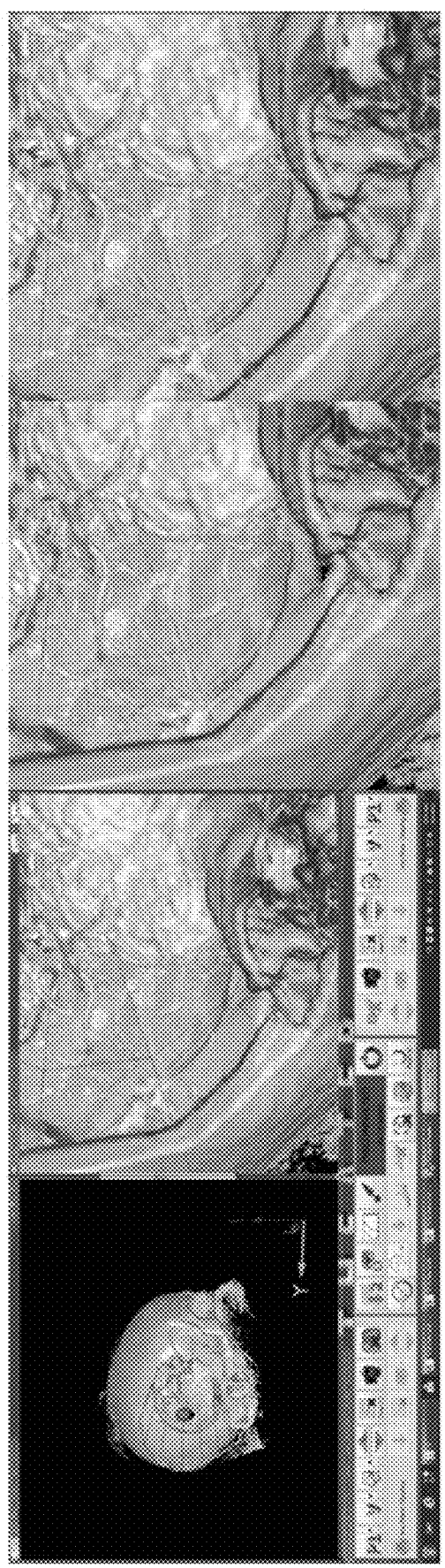
FIG. 6 illustrates an example view of a tumor case from inside the corridor down left.
Figure 7:
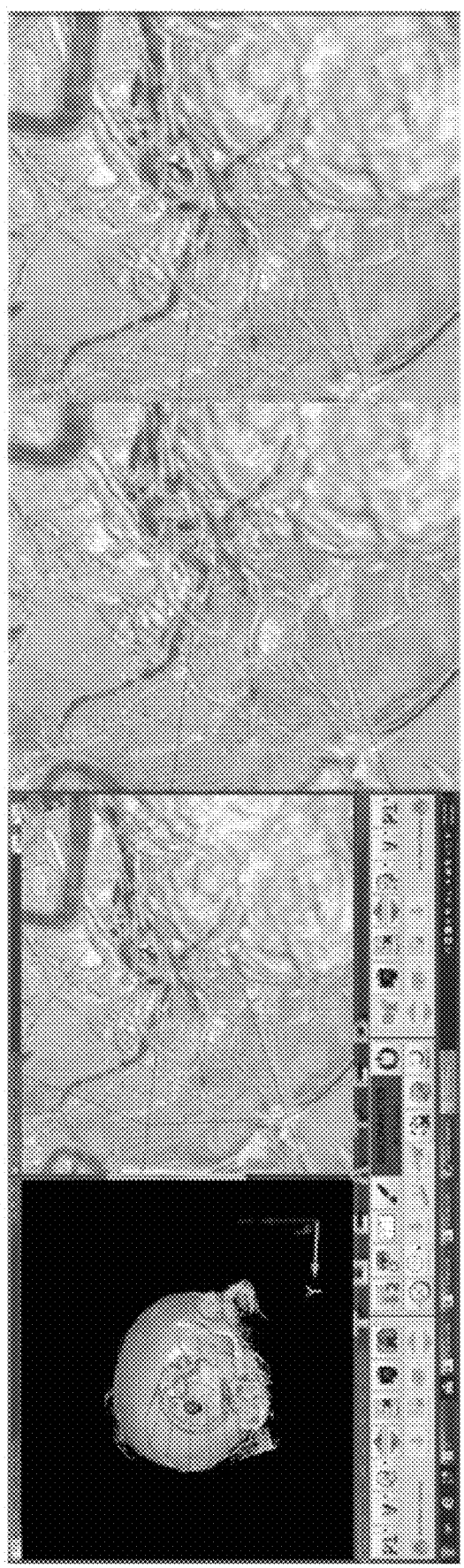
FIG. 7 illustrates an example view of a tumor case from inside the corridor left.
Figure 8:
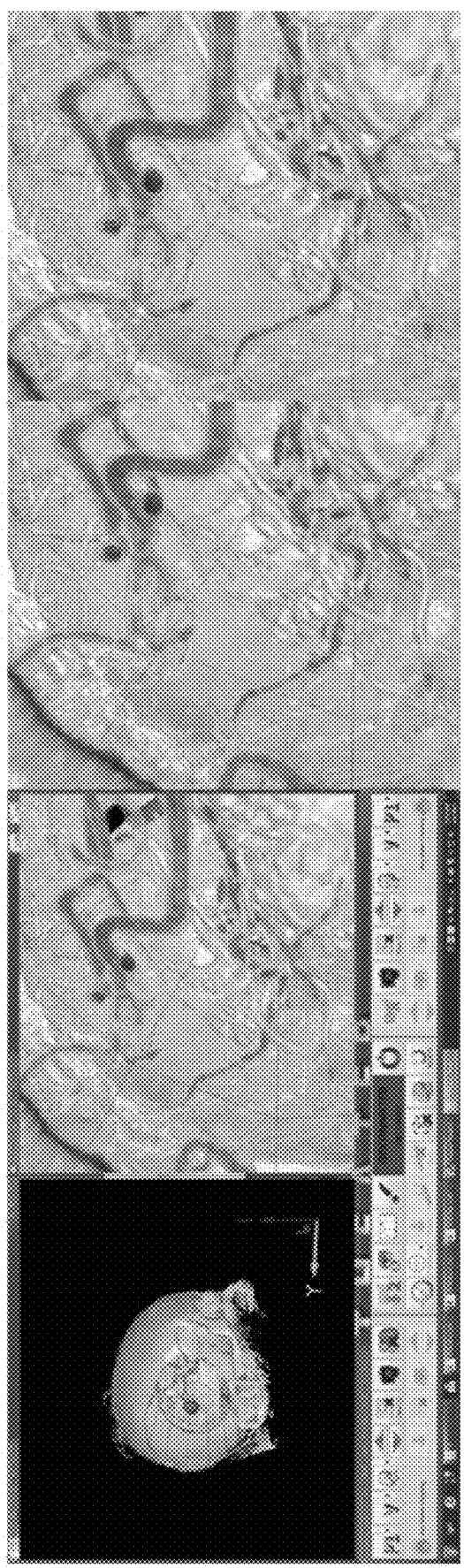
FIG. 8 illustrates an example view of a tumor case from inside the corridor left up.
Figure 9:
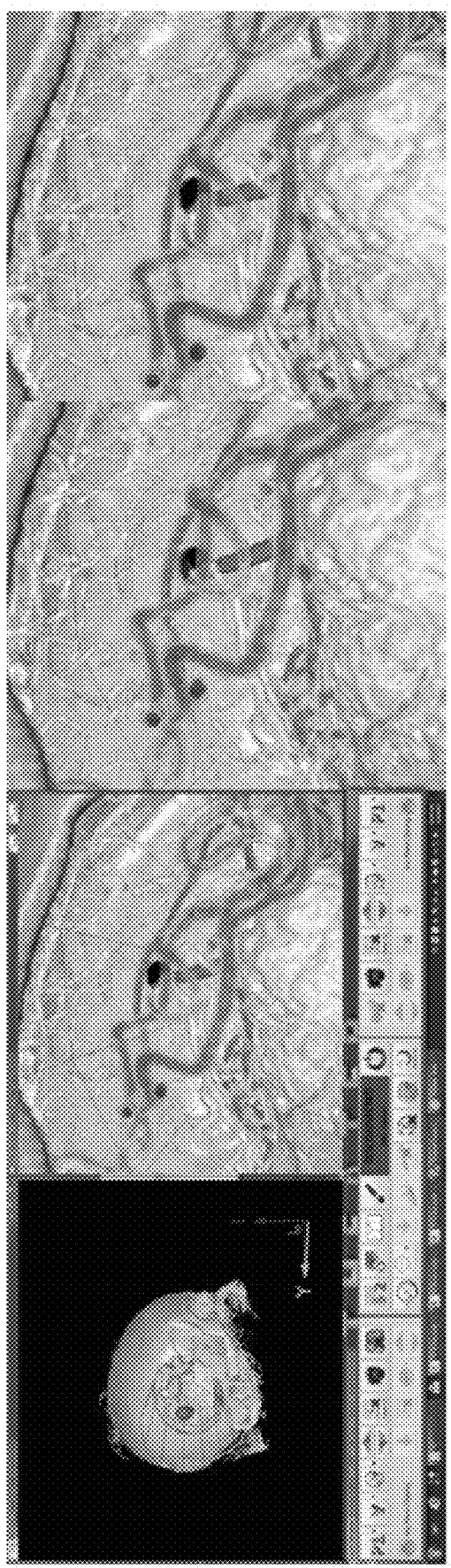
FIG. 9 illustrates an example view of a tumor case from inside the corridor up.
Figure 10:
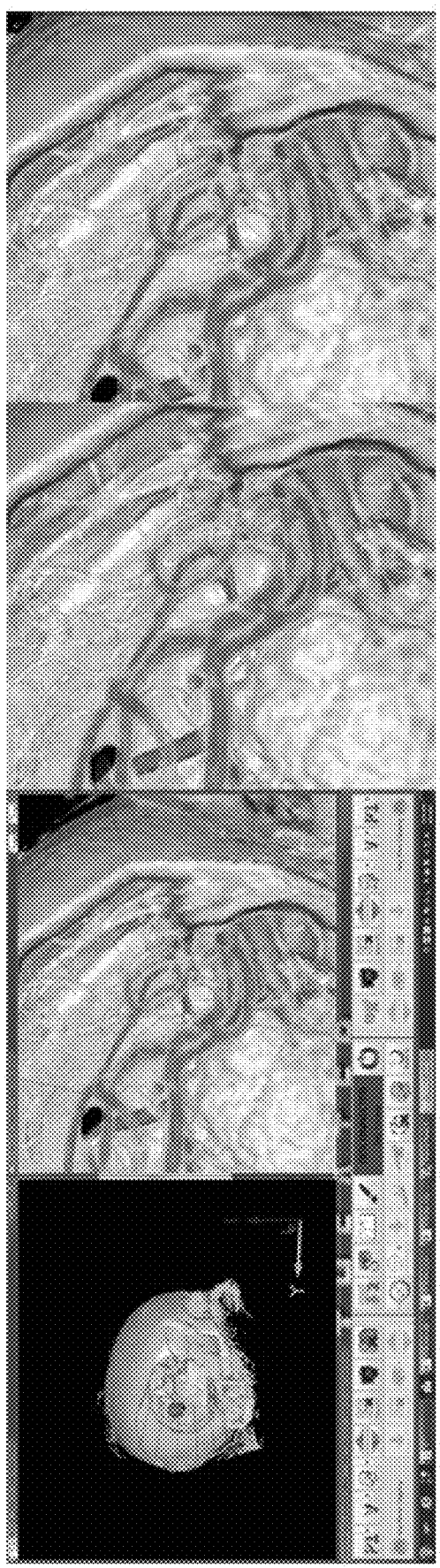
FIG. 10 illustrates an example view of a tumor case from inside the corridor up right.
Figure 11:
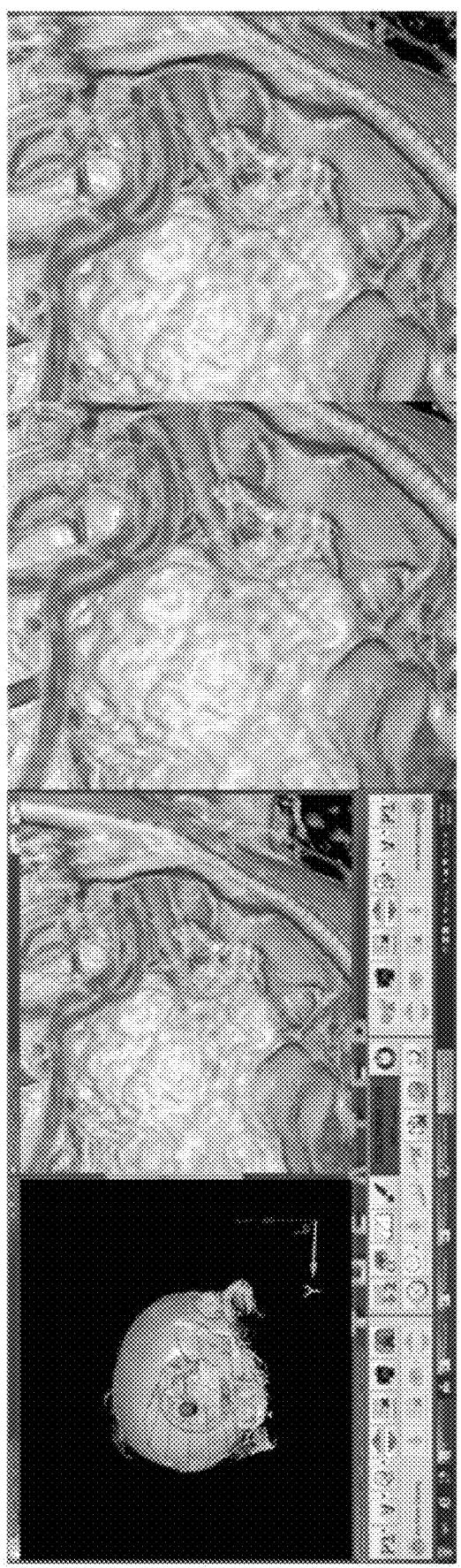
FIG. 11 illustrates an example view of a tumor case from inside the corridor right.
Figure 12:
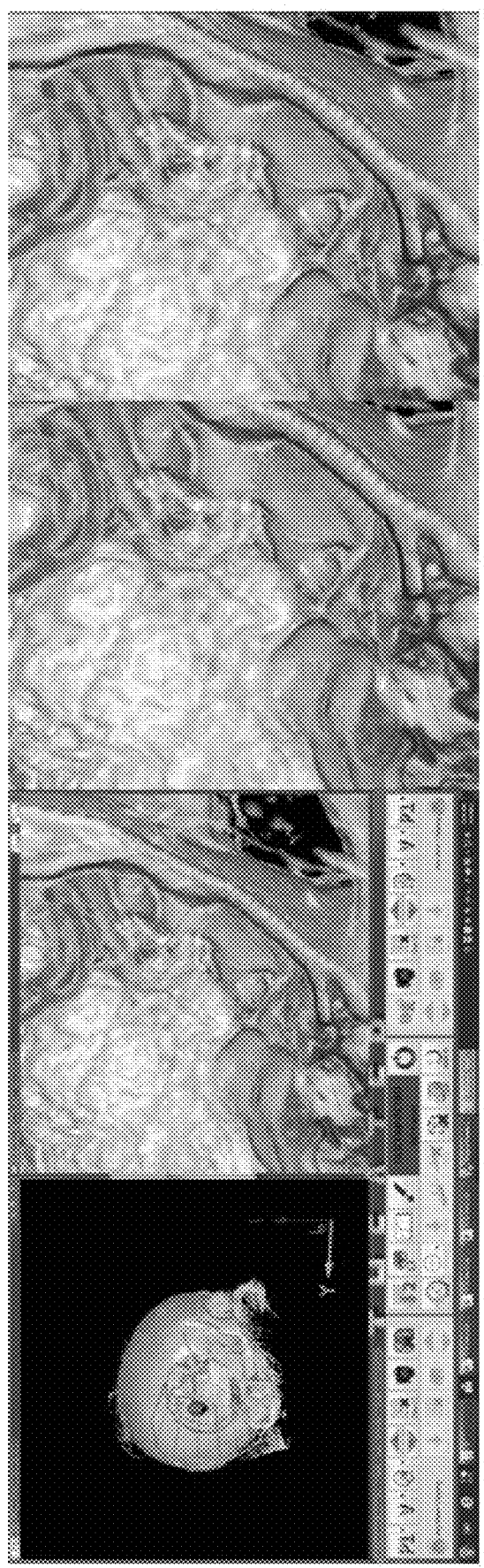
FIG. 12 illustrates an example view of a tumor case from inside the corridor right down.

External viewers are able to watch the surgeon's 102 virtual experience on the display monitor 108, which mirrors what the surgeon 102 is seeing and is continuously adjusted in real time to the movements being made by the surgeon 102. The display monitor 108 will reflect the user view on a single view 300, as illustrated in FIG. 4A, or as a 3D stereoscopic, side by side view 301, as illustrated in FIG. 4B, for monitors supporting 3D viewing.

In one example, external viewers see the user body and head positions, rotations, and movements represented as an Avatar positioned in the Scene on the display screen 108. In one example, the viewers are also able to interact with the Scene using a software interface, which will reflect on the Scene viewed by the user on the HMD 160'. Hence, the HMD incorporates the user (e.g., the surgeon) into the scene in an augmented fashion.

In AR mode, the surgeon 102 interacts with the SNAP Case in addition to the real world. The SNAP Case is positioned in a variety of specific locations to create an augmented world. The SNAP Case is virtually positioned at a surgeon-designated place in the real world environment. Potential positions include above the patient's bed, a table in the room, a 3D printed part of the patient, a tool with special markers, and any other suitable place in the room.

As part of this process, the location of the patient will be determined using any of a plurality of different means, such as by using sensors on or near the patient, video, or other mechanisms. Parts of the patient may be registered in the system and their locations monitored as desired to keep the displayed images accurate in relation to space and time.

If using a registration process, it will be shown on the registered anatomic part. For example, a 3D virtual image of a brain may be overplayed directly on top of a live video feed of the brain. In addition, using tracking information, the 3D virtual image is adjusted as the surgeon 102 moves the endoscope. In one example, the surgeon's 102 position is also tracked and, therefore, the 3D VR image may be adjusted and synched with the live video feed based on the surgeon's 102 position relative to the position of the patient 104. In other words, when the surgeon 102 moves his head or changes his position in the real world, the SNAP Case is virtually repositioned and reoriented to simulate it as a steady object in the real world. Voice commands or the Controller may allow for toggling between positions.

It should be appreciated that the system 100 allows visualization of tracked surgery tools in the OR. This is done through the use of information received by the system from other systems in the room, such as the Surgical Navigation System or other add-on sensors that may be separately provided, or integrated into the HMD. In one example, the HMD 160' may include one or more such sensors, which may include any or all of motion sensors, microphones, video sensors, cameras, accelerometers, location sensors, etc. In one example, one or more sensors may be positioned at a suitable location on the surgeon 102 or on input devices or other tools used by the surgeon 102.

External viewers are able to watch the primary user's or physician's 102 virtual experience on the display monitor 108 which mirrors what the user is seeing and is continuously adjusted in real time to the movements being made by the primary user. This window will reflect the user view on a single view or as a 3D stereoscopic, side-by-side view on monitors supporting 3D imaging, exactly as in VR mode.

It should be appreciated that a registration process may be required to align the SNAP Case received from the database 114 to a patient's anatomical scanned part or part viewed in a real time video feed via the endoscope. Alignment is based on the information retrieved from the patient's own pre-operative scans (upon which the SNAP case has been built), and the alignment/registration process information. In one example, alignment is achieved by receiving the registration information from a Navigation System in the operating room and aligning the case based on the received information. In another example, alignment is achieved by allowing the user to manually align it to the anatomical structure. This is done using the Controller. In another example, alignment is achieved by implementing the registration process using the Navigation Systems and align the result to the SNAP Case. In another example, alignment is achieved by using an IR Sensor to map the patient 104 head and align it to the SNAP Case automatically.

A typical clinical use case of the system 100 would be a neurosurgical intervention, for example, a tumor resection. In tumor cases, it would be possible to fly through the pre-planned surgical corridor, as illustrated in FIG. 4B, to the inside of the skull and look around in a CW direction including down, down left, left, left up, up, up right, right, and right down, as illustrated in FIGS. 5-12 respectively. The user can also fly behind the tumor and observe vessels that hug the tumor. In this case example, the clinical value is in the ability to see the displacement of posterior circulation vessels from their normal anatomical position as a result of the tumor. The user can fly along the surface of the tumor around to the front in order to perfectly appreciate the anterior circulation vessels and their displacement as a result of the tumor.

It should be appreciated that, although references throughout the description may be made to using the system 100 in connection with a surgical procedure for a brain tumor in particular, the system 100 may similarly be used on a variety of surgical applications on various anatomical parts of the patient 104.

Figure 13:
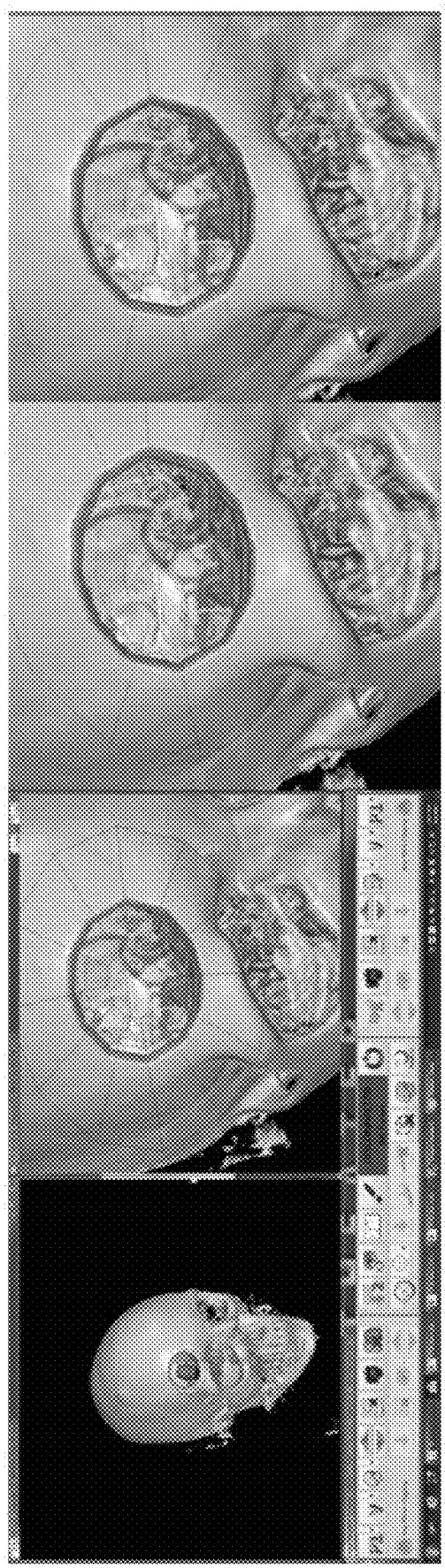
FIG. 13 illustrates an example view of an aneurysm case from outside the corridor.
Figure 14:
FIG. 14 illustrates an example view of an aneurysm case from inside the corridor.
Figure 15:
FIG. 15 illustrates an example view of an aneurysm case from inside the corridor down.
Figure 16:
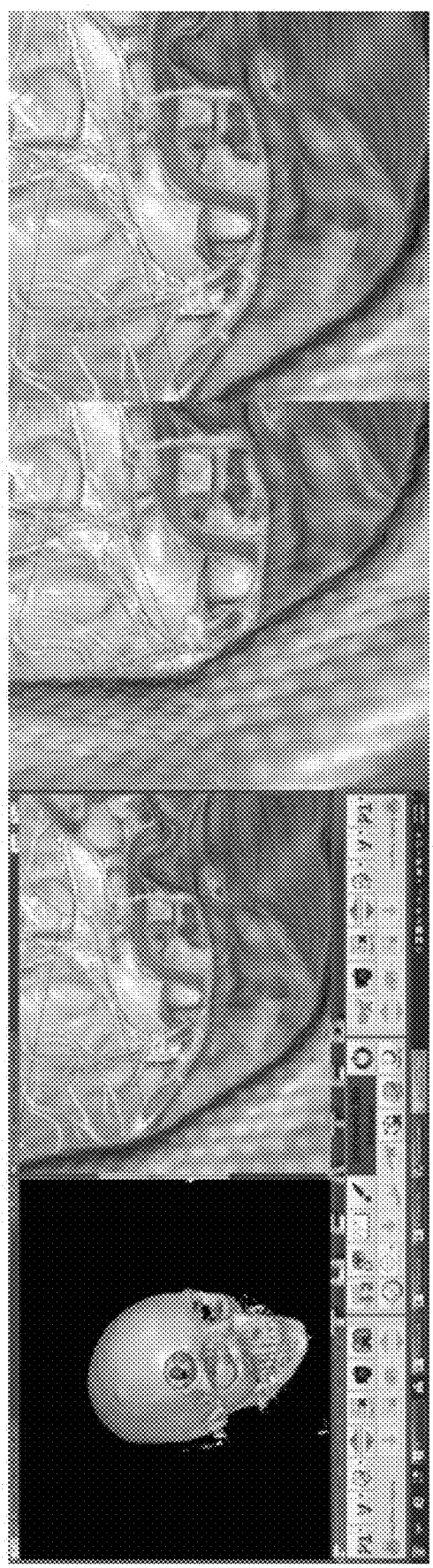
FIG. 16 illustrates an example view of an aneurysm case from inside the corridor down left.
Figure 17:
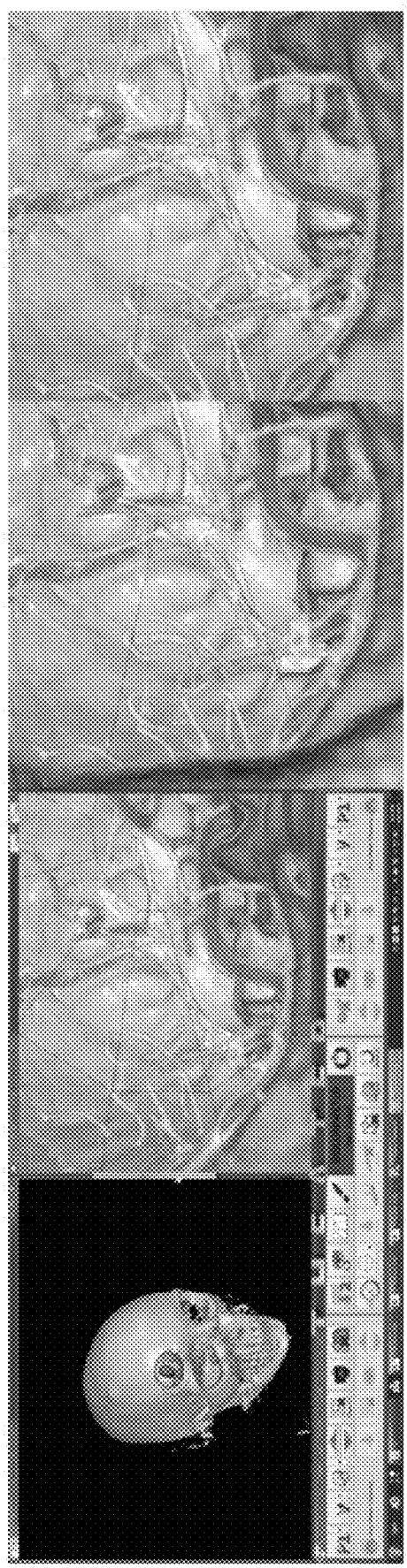
FIG. 17 illustrates an example view of an aneurysm case from inside the corridor left.
Figure 18:
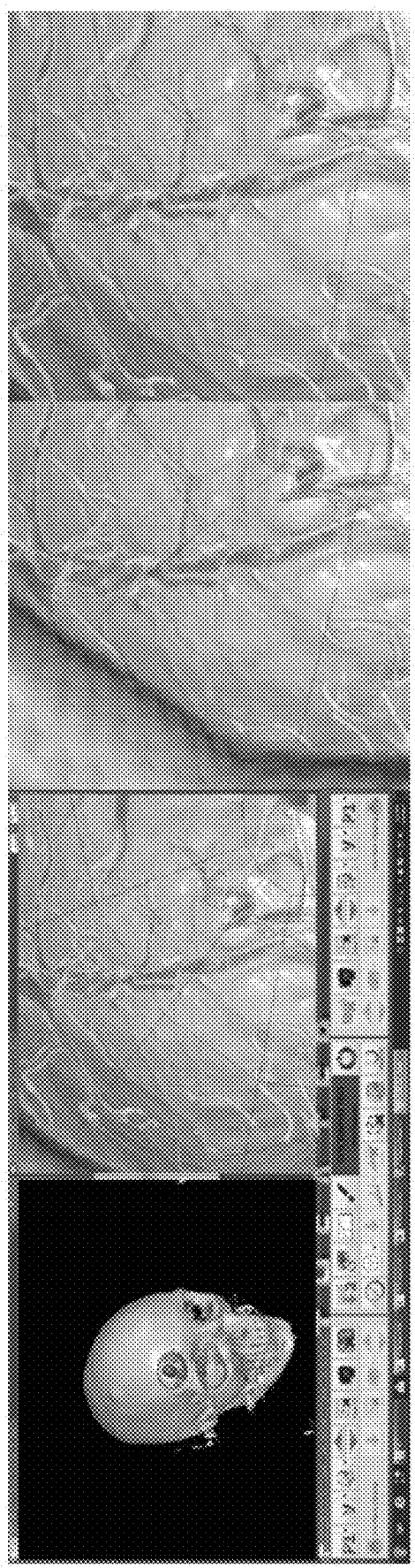
FIG. 18 illustrates an example view of an aneurysm case from inside the corridor left up.
Figure 19:
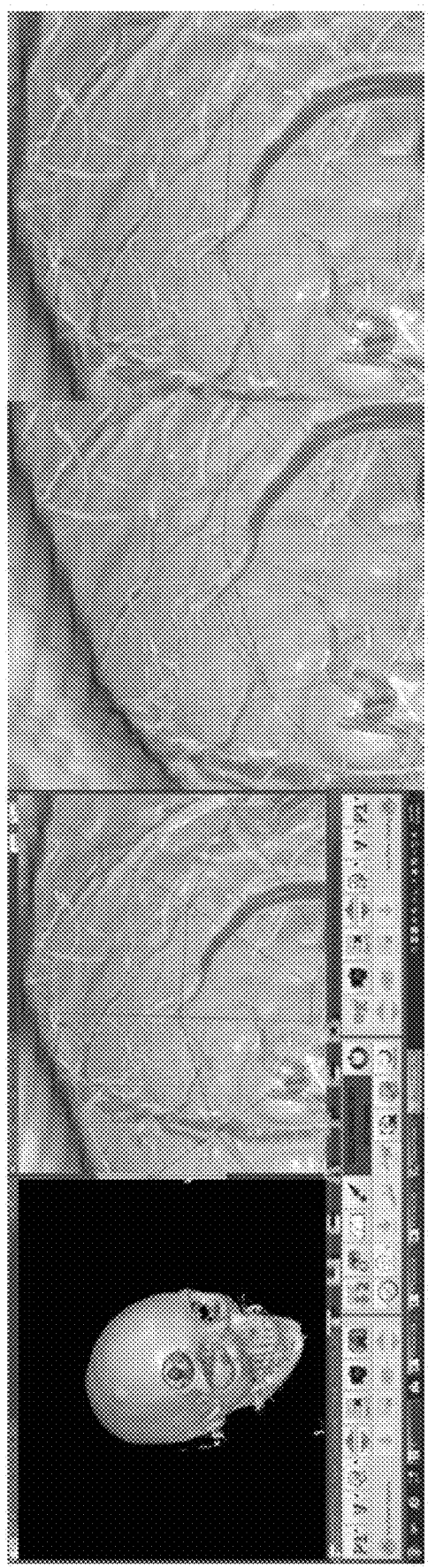
FIG. 19 illustrates an example view of an aneurysm case from inside the corridor up.
Figure 20:
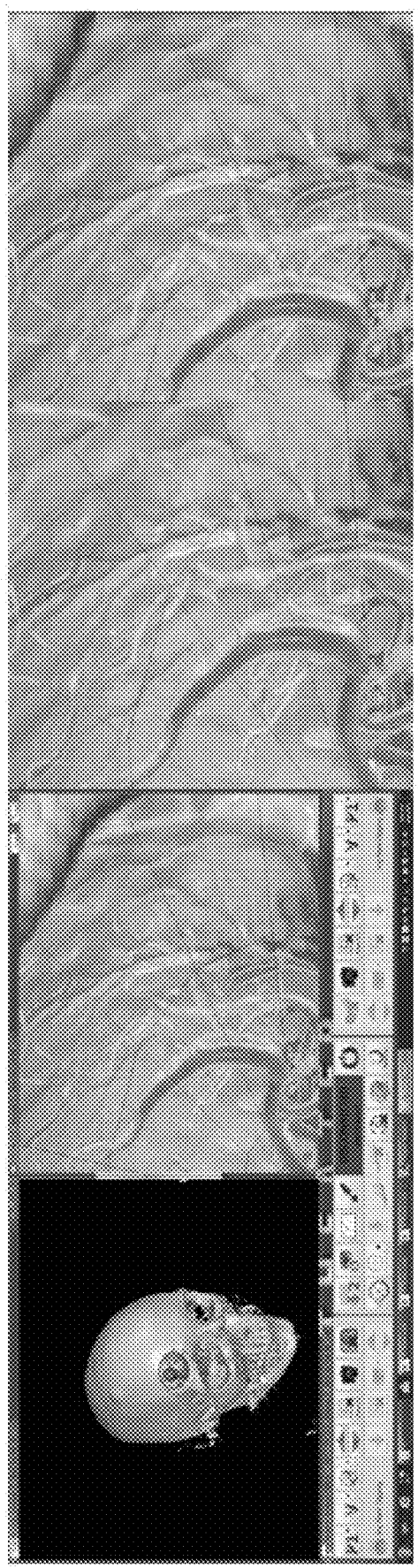
FIG. 20 illustrates an example view of an aneurysm case from inside the corridor up right.
Figure 21:
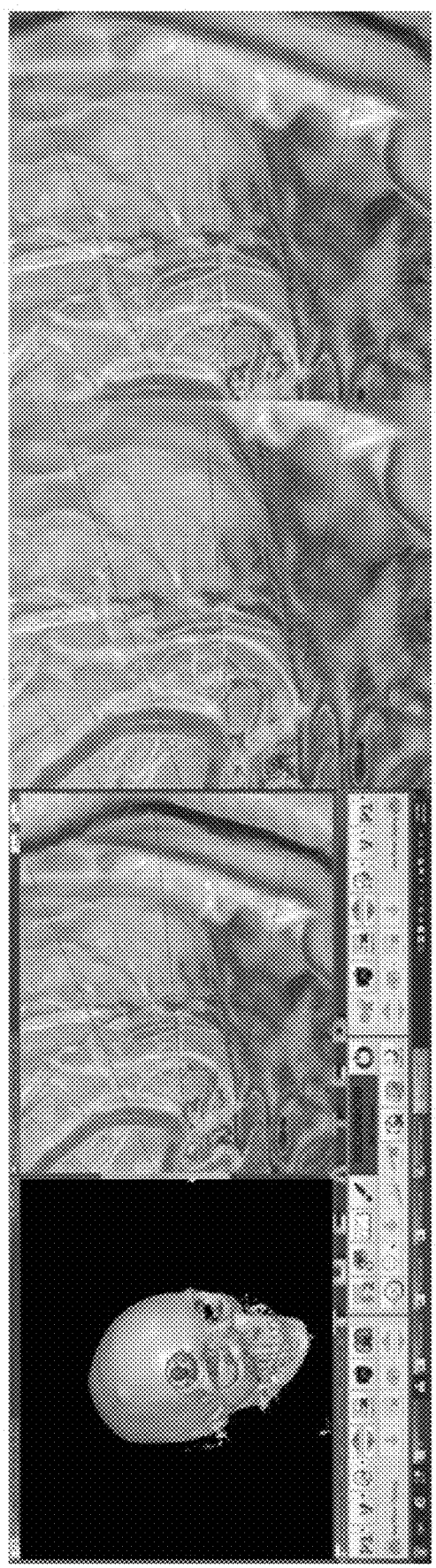
FIG. 21 illustrates an example view of an aneurysm case from inside the corridor right.
Figure 22:
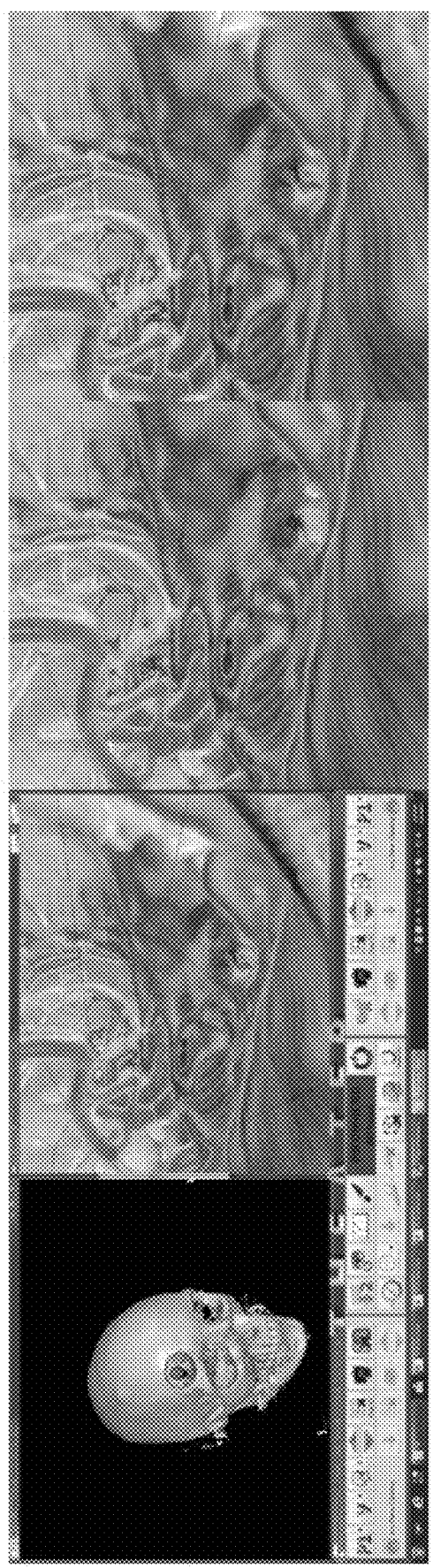
FIG. 22 illustrates an example view of an aneurysm case from inside the corridor right down.

For example, the system 100 can also be applied in neurovascular cases as well as tumor cases. In an example aneurysm case, the fly will start from outside the corridor, as illustrated in FIG. 13, and then move toward the craniotomy and stop just on the edge of the craniotomy looking forward, as illustrated in FIG. 14. Investigating the patient specific anatomy can then be achieved by navigating to the different views, including down, down left, left, left up, up, up right, right, and down right, as illustrated in FIG. 15-22, respectively. These views enable a surgeon to look for all the details surrounding the aneurysm. By utilizing a surgical planning tool, such as Surgical theater's Surgical Planner ("SRP") and the SNAP advanced VR capabilities with the library of 3D modeled aneurysm clips, the surgeon will be able to fly virtually inside the aneurysm site while evaluating and planning the 3D clip placement in the patient's actual anatomy. The surgeon will be able to observe the anatomical structures (i.e. neck, dome, etc.) and pathology with relation to the clip as if he was standing inside the patient's body. By moving his head up, down and around behind his shoulder, the surgeon is gaining a unique, never-before-available, immersive evaluation and planning of the procedure as if he was "touring" inside the patient pathology site.

Figure 23:
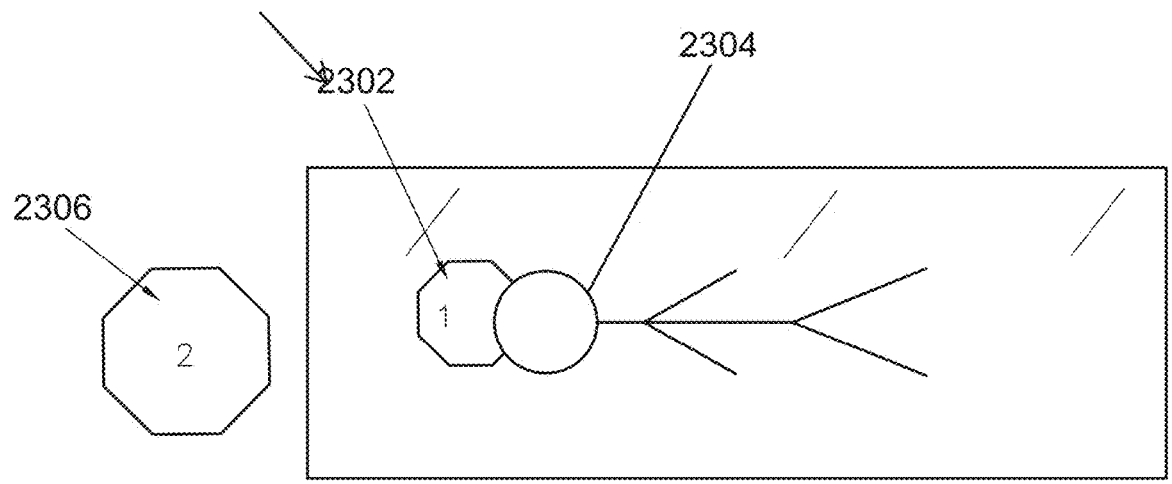
FIG. 23 illustrates an example top view in an operating room.

By connecting the SNAP to a tracking device, the "virtual navigation maneuvers" described can be done during a surgical procedure. In one example, as illustrated in FIG. 23, a sensor 2302 that tracks the orientation of the patient's head 2304 relative to the surgeon's position or point of observation 2306 and relative to the tools (microscope, endoscope, probe, etc.).

Figure 24A:
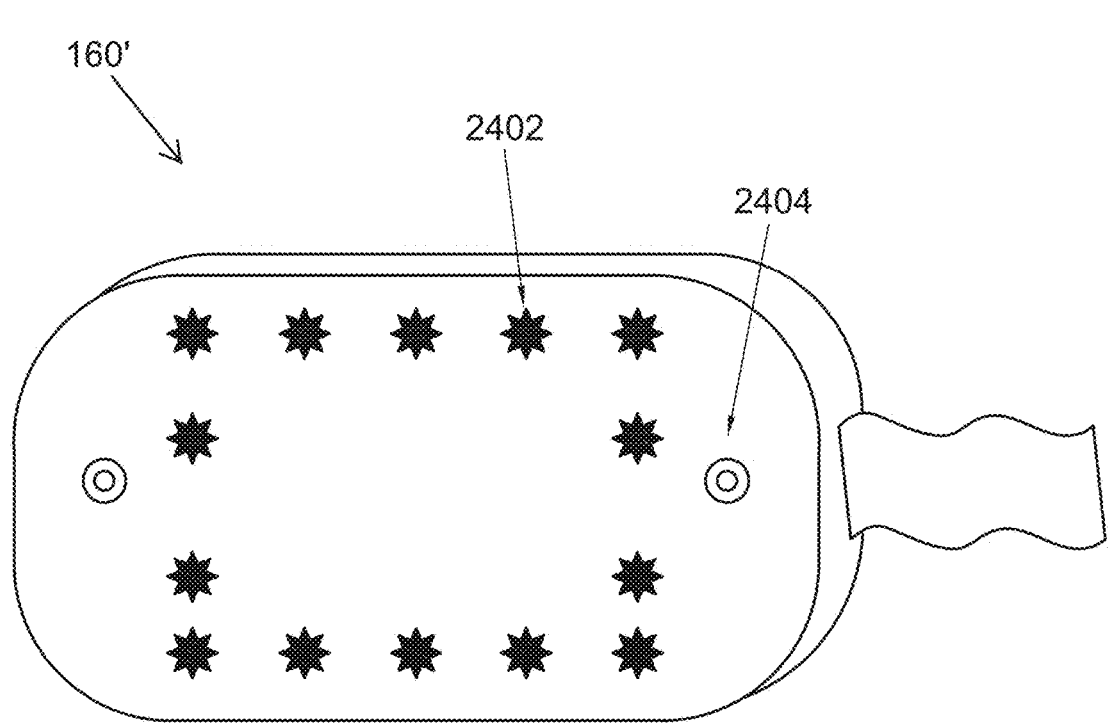
FIG. 24A illustrates a front view of an example head mounted display (HMD).
Figure 24B:
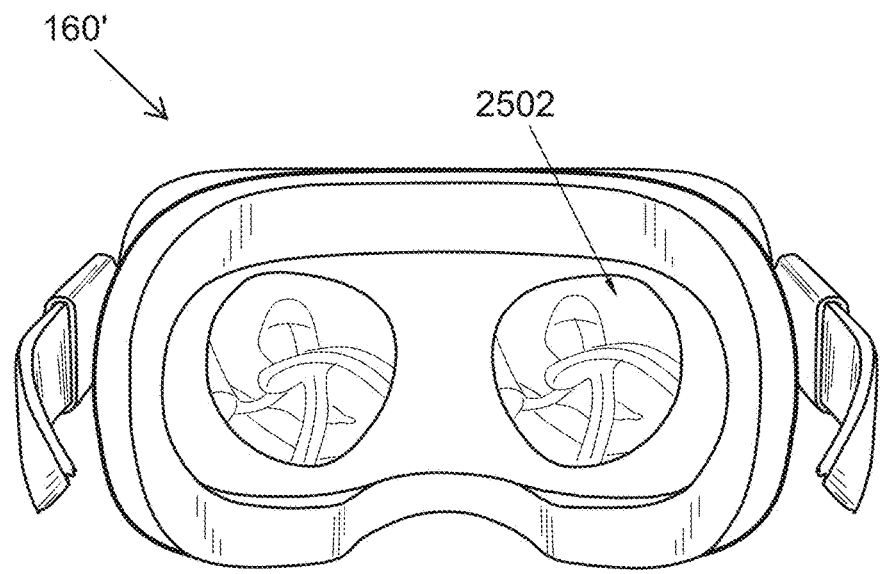
FIG. 24B illustrates a back view of an example head mounted display (HMD).
Figure 25:
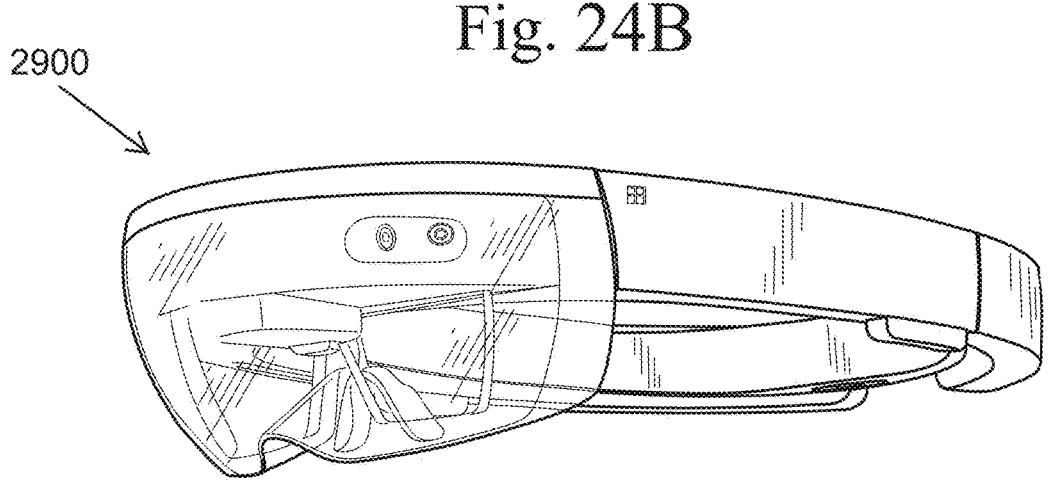
FIG. 25 illustrates another example head mounted display (HMD).

In one example, as illustrated in FIG. 24, the HMD 160' includes one or more sensors 2402 to facilitate tracking of the surgeon's point of observation. The HMD 160' displays 2502 all the information the surgeon will need during the surgery, as illustrated in FIG. 25A. In particular, the surgeon can access live video from his point of view (via an Endoscope, microscope etc.), as well as see the scans and the MD6DM model. He is able to get an augmented reality view that is combining the live view from his point of view of live surgical site with the patient specific MD6DM Model, as was illustrated in FIG. 2.

Referring again to FIG. 24, it should be appreciated that the orientation of the anatomical structures (i.e. head, brain, knee, shoulder etc.) is marked and pre-registered both in the physical patient and the scanned medical image (CT, Mill, Ultrasound, X-ray etc.). Therefore, the orientation of the scanned medical image and the real anatomical structures of the patient being evaluated in surgery are synchronized and aligned. Furthermore, as lenses and optic components improve, the HMD 160' may have, in one example, a built-in HD optical system 2404 (microscope, camera etc.) that will be synchronized and aligned with all the scanned images and the MD6DM. This allows for the elimination of the traditional surgical microscope, and the current limitations of those systems. Without changing glasses and loops, a larger number of surgeons can collaborate "under microscope" conditions using individual HMD's and head docking stations above the real patient. Head docking stations serve to keep the very intricate scenes steady for direct operators in critical microsurgical environments, while allowing external viewers to appreciate the exact same AR-enhanced "under scope" scene.

Referring again to FIG. 1, the system 100 further may include a controller 116, similar to the PlayStation, Xbox, PC games etc. controllers, although it should be appreciated that the controller 116 may be any suitable controller. Other possible controller types include an AR controller that will be screened on the HMD 160', gesture recognition interfaces, or speech recognition controller, etc. The surgeon 102 uses these different controllers 116 to move between the system options and screens.

Figure 26:
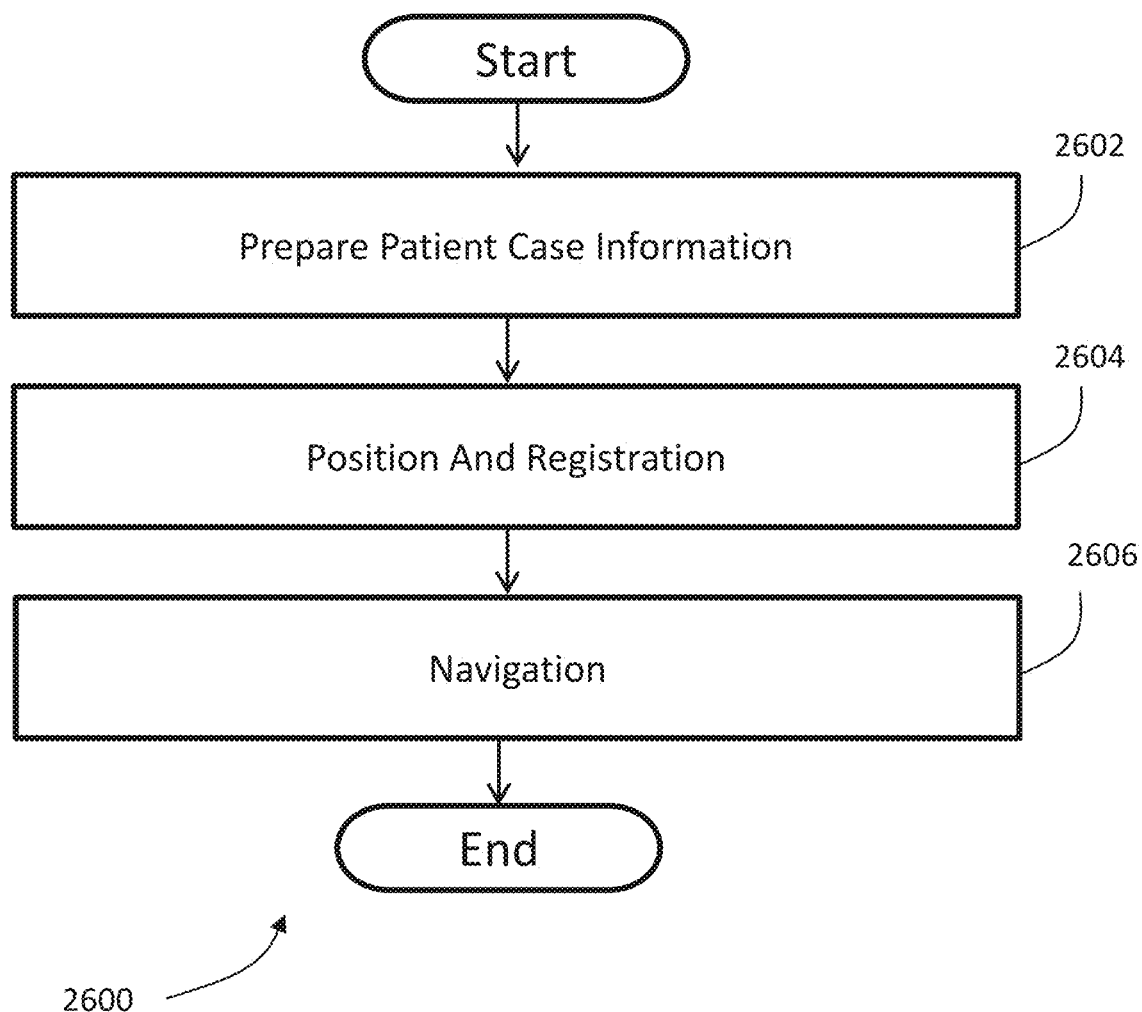
FIG. 26 illustrates an example Augmented Reality Surgical Navigation method

The system 100 will be further appreciated with reference to a method 2600 of use illustrated in FIG. 26. At step 2602, case information is prepared. In particular, the patient specific DICOM (CT, MRI etc.) data is uploaded into the SNAP computing device 112 and is processed to create the MD6DM. The MD6DM that has been created by the SNAP computing device 112 can also be edited by a clinical support technician or by the surgeon 102 himself. A technician can adjust the models to reflect specific surgeon preferences or intent. The technician can adjust the tissue segmentation, modify tissue-specific intensity ranges applied to the patient data, or change the transparency of the tissues. The surgeon 102 can also edit the model at any time during the preparation or operation. He can fuse multiple DICOM data sets that are part of the MD6DM such as CT and DTI or CT, MRI and DTI, or any other data set that has been uploaded into the SNAP computing device 112, including intraoperative images. The surgeon 102 can mark or highlight the volume of interest in several different ways. Furthermore, the volume of interest is not limited to the cranium and can be used for other parts of the body. Provided the DICOM data sets contain enough information (1 mm slice thickness or less), and are collected in a volumetric acquisition, any part of the anatomy imaged can be modeled. Preparation continues until the case information is ready and the surgeon 102 is pleased with the views prepared.

At step 2604, during position and registration, the SNAP computing device 112 matches or co-registers between the real organism, for example the head in neurosurgery, the system 100 sensors, the DICOM scans, and the MD6DM. The registration or "matching" process gives the ability to navigate during the surgery. It is important to do this mapping process in the beginning of the surgery when all of the equipment is being brought in and the patient is being positioned for surgery. The mapping can be done by several methods. Methods are dependent on the navigation system manufacturer and include surface base registration, scanning the face of the patient, or by point-based registration, which involves touching points on the patient's head according to the system guidance. Different manufacturers use different types of sensors to do registration, and SNAP with MD6DM can work with any of the methods and sensors.

Once registration is done, navigation in real time at step 2606 is possible. In particular, the surgeon 102 puts on the HMD 160'. He will get a live video picture from his point of view (built-in camera). By utilizing the controller 116, the surgeon is able to perform a number of navigation functions, including: zooming in and out; adding traditional scanned views, including moving between the views and zooming in and out; adding an MD6DM model view, including walking around the model, simulating and deciding trajectory, and looking behind the pathology; and navigating in augmented reality view. The real time navigation functions are enabled by the ARS computing device 112 which leverages the tracking information and combines a live video feed with predefined scans and models to render images to be delivered to the surgeon based on the surgeon's movements and actions.

Using navigation, the surgeon 102 is able to determine an optimal approach to avoid major vessels. He can view the real worldview and the MD6DM model side by side under the HMD 160' from the same direction. In an example application of treating meningioma, the surgeon 102 is able to look behind the meningioma and to see the influence the pathology has had on the patient's anatomy. On the MD6DM, the surgeon 102 is able to visualize the boundaries of the tumor while he is resecting the meningioma and can see how far he is from vessels or other vital structures.

In another example application, the surgeon 102 is able to perform an aneurysm clipping using an endoscopic approach. Before skin incision and craniotomy are made, the surgeon 102 consults the MD6DM and determines the trajectory to avoid major vessels and other significant structures. After marking the craniotomy (key hole), he will start the incision. The surgeon 102 now uses the endoscope 106 for the surgery. On the HMD 160', the view from the endoscope camera is augmented with the simulated endoscope view of the prebuilt model. Alternatively, the surgeon 102 can get side-by-side endoscopic camera view and the model with the orientation of the endoscope 106. Sensors in the system move the model point of view according to the movements of the surgeon 102 so that the model and real-time view remain aligned. The surgeon 102 can move between the views in order to achieve the most minimally invasive approach while avoiding damage to other critical structures.

In another example, the surgeon 102 can use the ARS 100 for neurovascular pathologies like aneurysms or arteriovenous malformations (AVMs). Before or after the registration step 2604, trajectory can be determined or confirmed prior to craniotomy incision. The surgeon 102 can use the patient specific case model to determine which approach, endoscopic or open, is most appropriate. After registration, the surgeon 102 will use the HMD 160' or other VR display to dissect down to the aneurysm while alternately looking on the endoscopic/camera view side by side to the model. As described above, the ARS system 100 knows through sensor input to rotate and adjust the model so it remains aligned with the surgeon's 102 view. When the aneurysm is reached, the surgeon 102 is able evaluate the aneurysm neck, as well as get a 360 degree view around the aneurysm in the AR model. For additional precise planning, the surgeon 102 can virtually apply different clips to the aneurysm to help ensure appropriate clip sizing.

Figure 27:
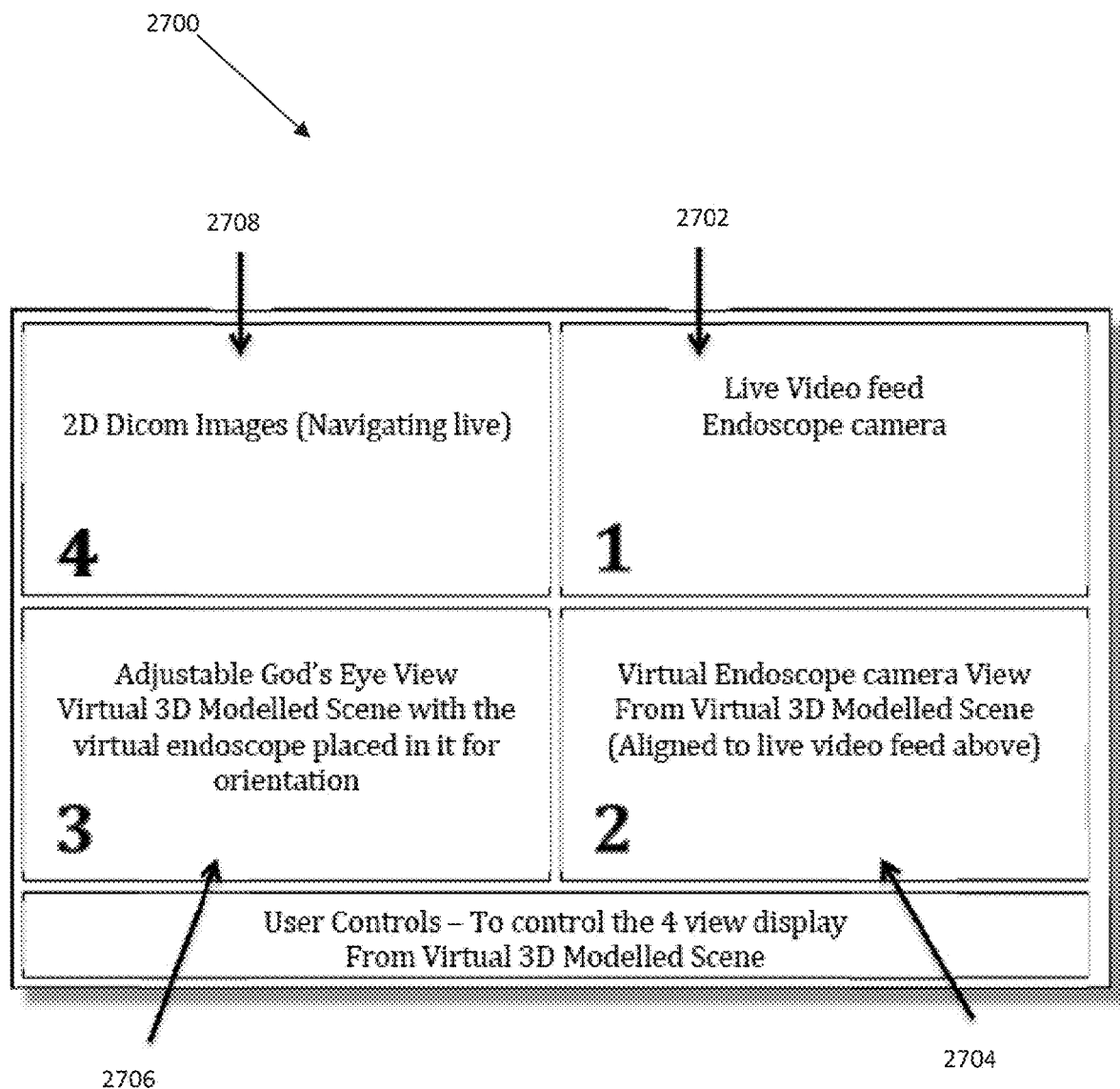
FIG. 27 illustrates an example optical 4-view display format.

It should be appreciated that the system 100 described herein allows the surgeon 102 to perform endoscopic surgery with increased situational awareness. The operator has a 4-view display 2700, as illustrated in FIG. 27, that presents the surgeon with the following information which can be displayed either on the display monitor 108 or via the HMD 160': a live video feed from the endoscope camera view 2702; a live virtual video feed from the virtual reality camera of the endoscope in the SNAP 3D patient specific modeled scene 2704; an adjustable "God's Eye View" of the virtual patient specific 3D modeled scene (anatomy with pathology) of the SNAP 2706, with a virtual endoscope tool displayed in the correct location and orientation with respect to the patient's anatomy; and a live 3 panel view 2708 of the 2D DICOM images (Axial/Coronal/Sagittal) with the slices adjusted in all views to the current endoscope tip location.

The virtual endoscope view 2704 is aligned to the real endoscope camera 2702 in both position and orientation, as well as camera parameters (Zoom, Field of view, etc.). It should be appreciated that the surgeon 102 has the ability to control the virtual endoscope camera 2704 with head vector adjustments to perform look right/left/up/down. This allows him to disengage the virtual camera 2704 from the real camera 2702, and look around for better situational awareness. In addition, the surgeon 102 has the ability to adjust the God's Eye View (an orienting high level view of the whole scene) to define his preferred angle of view of the scene, with adjustable scene clipping and tissue segmentation.

In one example, when the virtual camera view 2704 is not aligned to the real camera 2702, the user sees markers on the virtual camera view 2704 showing him how much the offset is from the real camera 2702.

It one example, the 4-screen output 2700 displayed on the HMD 160' is adjustable by the user. In particular, the surgeon 102 is able to toggle between all four (4) screens at once and any of the four (4) maximized on the display for full view.

It should be appreciated that there are many systems in the operating room which track the user status during surgery. Accordingly, in one example, the AR HMD 160' will allow the user to visualize information from those systems and also get notifications from outside the operating room unless muted. This allows the user to remain focused on the surgery while still being able to process needed information during surgery, without taking his eyes off of the patient.

In one example, the system 100 integrates with video systems in the operating room which allows others in the OR to see what the user is seeing in his HMD 160'.

In one example, the system 100 and method 2600 described herein may be used in a collaboration mode. In this mode, the surgeon 102 can choose to allow other remote users to join the Scene when desired. Users may communicate with remote users as follows: 1) Headphone/Speaker are used to hear all other remote users; 2) a Microphone is used to talk to all remote users; and 3) the video stream includes one of two forms: in AR mode the augmented view the users sees on the HMD 160' will be the video streamed to other remote users, while in VR mode the user can choose, using a controller 116, to see what other remote users see, or to change their view to his own view.

Figure 28:
FIG. 28 illustrates an example of multiple users represented as Avatars in an example Scene.

As illustrated in FIG. 28, while in collaboration mode, the other users in the Scene will be viewed as Avatars 2802 which will show other users' positions, head and body movement.

In order to communicate with the user and the Scene during collaboration mode, several features are available, including: 1) a headphone/speaker to hear all other remote users; 2) a microphone to talk to all remote users; 3) a hand tracker for tracking the hand movements and presenting them on the Scene (each user may be represented as a different color); 4) 3D markers to select and mark areas in the Scene; and 5) an avatar wherein the other users in the Scene will be viewed as Avatars which will show other users position, head and body movement.

In an example application of the collaboration mode, a user in the OR planning a craniotomy based on the SNAP Case (after registration) is able to open a video transmission from his AR HMD 160' to a remote surgeon to consult or get feedback on his planned approach. The surgeon collaborator is able to visualize what the surgeon 102 in the OR is seeing on a remote system. The remote surgeon is also able to interact with the Scene and virtually mark areas through hand movements and virtual tools.

In one example, an "explorer" mode is available. In this mode, points will be predefined and placed with following numbers in the scene. When the explorer function is activated, the user will automatically be virtually driven between those pre-planned points as if they were in the back seat of a car. The user has the ability to rotate his head and evaluate the structures around him as he is being slowly taken through the points.

Such an explorer mode may be available for training in collaboration mode and also during endoscopic surgery. In particular, the user will be able to freeze his position and discuss as he goes through his pre-defined explorer path, a functionality particularly useful in educational settings for testing comprehension. During endoscopic surgery, the ability to reach pre-planned points of anatomy eliminates the need to swap the endoscope and surgical navigation probe in and out of the body to continuously check position and trajectory during dissection, potentially shortening surgery.

In one example, a tracking system will track all the tools and movements in the OR and record. This allows for users outside of the OR to see what the surgeon 102 is doing virtually, both with fine instrument movements and gross head/body movements. It also allows the direct operating team to debrief what the surgeon 102 did during the surgery and gives the surgeon 102 a way to evaluate and critique his own movements during the case.

It should be appreciated that any suitable type of head mounted display (HMD) 160' may be used with the system 100. FIG. 25B illustrates on alternative example of a HDM 2900. HDM 2900 includes a wireless antenna (not shown), for example. Accordingly, the HDM 2900 may operate wirelessly and therefore eliminate the need for extra cords in the operating room.

HDM 2900 further includes a processor and memory (not shown). Thus, in one example, the HDM 2900 may be configured to receive, store, and process MD6DM models without relying on an ARS computing device 112. For example, the HDM 2900 may be preloaded with the appropriate MD6DM model or models relevant for a specific patient and procedure before entering an operating room. This offers a lot more flexibility and mobility within the operating room without the need to bring in extra equipment into an already crowded room.

In one example, a HDM 2900 may not have sufficient memory or processing capabilities to store and process a full MD6DM model. Thus, in one example, the ARS computing device 112 may be configured to generate light or stripped down versions of an augmented reality models and transfer the light versions to a HDM 2900 before the surgeon takes the HDM 2900 into the OR. For example, if a certain layer of detail of a brain is not necessary for performing a certain procedure, that layer of information may be removed from the model, thereby creating a lighter version that may more easily stored and processed on the HDM 2900.

It should be appreciated that the example system and method described herein may be scaled in several ways. For example, although the example system and method may have been described with reference to a single HDM, it should be appreciated that the system may comprise multiple surgeons or users with multiple HDMs within an operating room during a surgery, all relatively simultaneously receiving their own custom augmented reality experience based on their location and orientation within the room. In addition, remote users not present in the OR at the time of the surgery, or even a user that is present in the OR, may experience an augmented reality experience from the perspective of one of the other users in the OR.

In one example, an operating room may include multiple cameras or sensors placed around the room in order to track a user wherever the user is positioned. Thus, rather than being limited to a specific side or section of a patient, a user may walk 360 degrees around the patient during a surgery and experience the augmented reality image anywhere in the room from any side or angle of the patient.

In one example, additional input sources may be integrated into the augmented reality experience that may be suitable for providing a surgeon with appropriate information that may be helpful to reference during surgery. For example, a surgeon may have an additional camera mounted on headset that may provide another perspective live video feed that can be augmented, in addition to the video feed received from the endoscopy. In another example, the additional camera may be a floating camera, either mounted at some fixed location in the operating room or moveable about the room.

Figure 33:
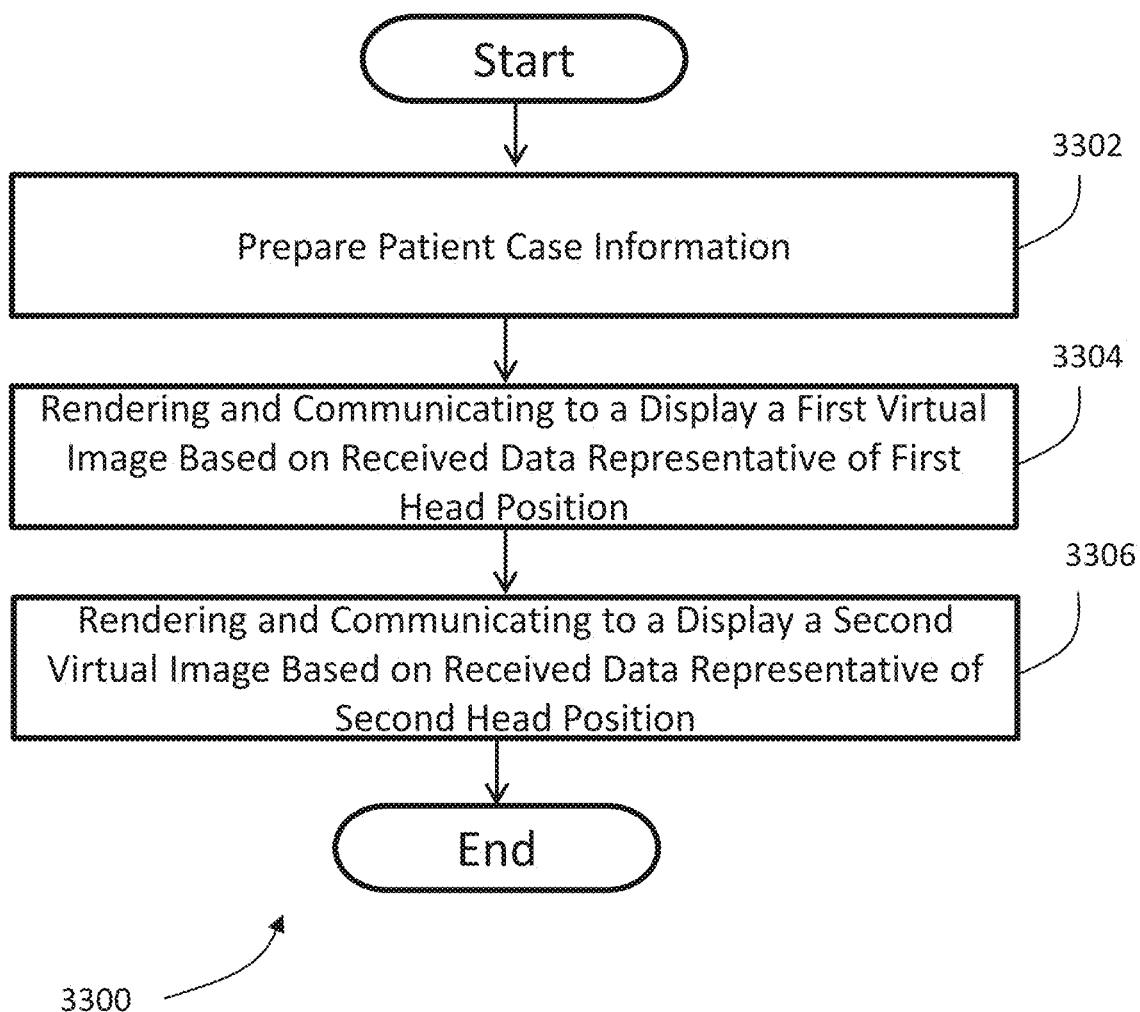
FIG. 33 illustrates an example Augmented Reality Surgical method.

The system 100 will be further appreciated with reference to a method 3300 of use illustrated in FIG. 33. At step 3302, patient case information is prepared. At step 3304, a first virtual image is rendered and communicated to a display, wherein the first virtual image is based on received data representative of a first head position. At step 3306, a second virtual image is rendered and communicated to the display, wherein the second virtual image is based on received data representative of a second head position.

Figure 30:
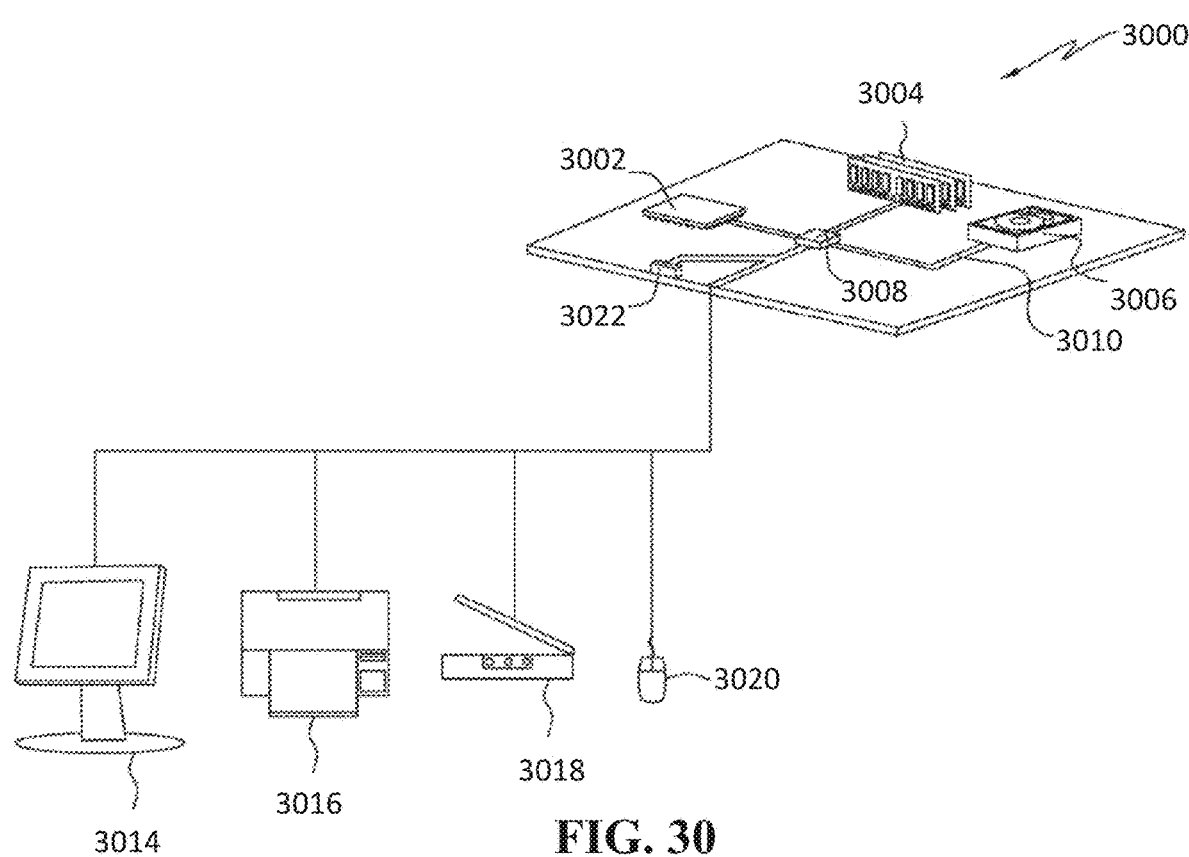
FIG. 30 is a schematic diagram of an example computer for implementing the example ARS computing device of FIG. 1.

FIG. 30 is a schematic diagram of an example computer for implementing the example AR computing device 112 of FIG. 1. The example computer 3000 is intended to represent various forms of digital computers, including laptops, desktops, handheld computers, tablet computers, smartphones, servers, and other similar types of computing devices. Computer 3000 includes a processor 3002, memory 3004, a storage device 3006, and a communication port 3008, operably connected by an interface 3010 via a bus 3012.

Processor 3002 processes instructions, via memory 3004, for execution within computer 3000. In an example embodiment, multiple processors along with multiple memories may be used.

Memory 3004 may be volatile memory or non-volatile memory. Memory 3004 may be a computer-readable medium, such as a magnetic disk or optical disk. Storage device 3006 may be a computer-readable medium, such as floppy disk devices, a hard disk device, optical disk device, a tape device, a flash memory, phase change memory, or other similar solid state memory device, or an array of devices, including devices in a storage area network of other configurations. A computer program product can be tangibly embodied in a computer readable medium such as memory 3004 or storage device 3006.

Computer 3000 can be coupled to one or more input and output devices such as a display 3014, a printer 3016, a scanner 3018, and a mouse 3020.

While example systems, methods, and so on, have been illustrated by describing examples, and while the examples have been described in considerable detail, it is not the intention to restrict or in any way limit the scope of the appended claims to such detail. It is, of course, not possible to describe every conceivable combination of components or methodologies for purposes of describing the systems, methods, and so on, described herein. Additional advantages and modifications will readily appear to those skilled in the art. Therefore, the invention is not limited to the specific details, and illustrative examples shown or described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

Many other example embodiments of the invention can be provided through various combinations of the above described features. Although the invention has been described hereinabove using specific examples and embodiments, it will be understood by those skilled in the art that various alternatives may be used and equivalents may be substituted for elements and/or steps described herein, without necessarily deviating from the intended scope of the invention. Modifications may be necessary to adapt the invention to a particular situation or to particular needs without departing from the intended scope of the invention. It is intended that the invention not be limited to the particular implementations and embodiments described herein, but that the claims be given their broadest reasonable interpretation to cover all novel and non-obvious embodiments, literal or equivalent, disclosed or not, covered thereby.

What is claimed is:

1. A virtual reality surgical navigation method, comprising the steps of:
   obtaining medical images associated with anatomy inside a particular patient;
   preparing a multi dimension virtual model from the medical images associated with the anatomy inside of the patient;
   receiving position data for a particular location within the patient;
   receiving position data indicative of a user's current direction of view from a position sensor, said position sensor configured to directly detect a location or motion of the user or a physical feature of the patient, said position data including direction of view;
   rendering, by executing software instructions on a computer system, an initial virtual three-dimensional image from the virtual model, the virtual three-dimensional image being representative of an anatomical view of the patient from an initial perspective at the particular location inside the patient, wherein the perspective is determined by data indicative of the user's current direction of view and the particular location, wherein
   the anatomical views of the initial perspective at the particular location can be changed by changing to different directions of view of the user;
   receiving an input to move the particular location to an arbitrary new location within the patient;
   rendering, by executing software instructions on the computer system, an updated virtual three-dimensional image from the virtual model, the updated virtual three-dimensional image being representative of an anatomical view from an updated perspective at the new location inside the patient, wherein the updated perspective is determined by data indicative of the user's current direction of view at the new location; and
   capturing video data of anatomical features of the patient during execution of the method for use in rendering the virtual three-dimensional image, wherein
   the anatomical views of the updated perspective at the new location can be changed by changing to different directions of view of the user, wherein
   the rendered virtual images are continuously provided to a virtual headset display for display to the user.

2. The method of claim 1, further comprising the step of generating a virtual avatar for display in the virtual three-dimensional image showing the current location of the user's perspective as the location changes.

3. The method of claim 2, wherein a virtual model marker is provided in the rendered virtual three dimensional image such that the marker is configured to perform an action when the avatar are within a predefine proximity of the marker.

4. The method of claim 1, wherein the perspective of the user inside the patient can be changed by operation of a controller.

5. The method of claim 1, wherein the perspective of the user inside the patient can be changed by a change of location of the user's position.

6. The system of claim 1, wherein position data indicative of a user's current head position is determined by the position sensor included in a virtual headset display mounted on the head of the user.

7. The system of claim 1, wherein the input indicative of the user's desire to view the inside of the patient from the new location is generated by a sensor tracking the position of the user.

8. The system of claim 1, wherein the input indicative of the user's desire to view the inside of the patient from the new is generated by the user inputting data via a controller.

9. The system of claim 1, wherein the new location comprises a change in at least one of the X, Y, and Z coordinates of a three-dimensional coordinate system.

10. The system of claim 1, further comprising the steps of:
continuously, in real time, receiving updated position data from the position sensor as a user's head position changes and desired location inside the patient changes; and
continuously, in real time, rendering virtual three-dimensional image being representative of an anatomical view from a perspective and location corresponding to the updated head position and updated location.

11. The system of claim 1, wherein the virtual model is based on received patient specific DICOM data.

12. The system of claim 1, wherein the virtual model is configured to receive, synchronize with, and integrate into the virtual model, in real time, a live video feed.

13. The system of claim 12, wherein the live video feed comprises one of a microscope visual, an endoscope visual, or a robotic arm visual.

14. The system of claim 1, wherein the virtual model is configured to receive, synchronize with, and integrate into the virtual model, in real time, multiple avatars representative of multiple users' current relative position and simultaneous interaction with the virtual model.

15. The system of claim 14, wherein, wherein a marker is configured to perform an action that is responsive to an event that one of the avatars are within a predefine proximity of the marker.

16. The system of claim 15, wherein the action comprises at least one of changing colors, activating an audible alarm, and displaying additional information.

17. The system of claim 1, wherein the virtual model is configured to receive, synchronize with, and integrate into the virtual model, in real time, a manually created element generated by the user.

18. The system of claim 1, wherein the virtual model is configured to receive, synchronize with, and integrate into the virtual model, in real time, a generic anatomical model to enhance the anatomical view.

19. The system of claim 1, wherein the virtual model is configured to receive, synchronize with, and integrate into the virtual model, in real time, information for assisting the user in understanding pathology within the anatomical view.

20. The method of claim 1, wherein an endoscope camera is used on the patient to provide real-time patient organ data to support images in an augmented reality view as part of the three-dimensional image provided to the user.

21. The method of claim 20, wherein an image of said endoscope camera is included in said augmented reality view.

22. The method of claim 1, wherein said position sensor is mounted on a head mounted display worn by the user, and wherein said head mounted display provides a pass-through view of the patient to the user.

23. An augmented reality surgical navigation method, comprising the steps of:
preparing a multi dimension virtual model associated with a patient;
receiving tracking information from a position sensor, said position sensor configured to directly detect a location or motion of the user or a physical feature of the patient indicative of a user's current view of the patient at a particular location within or around the patient, said tracking information including the user's position relative to the patient and the user's angle of view of the patient;
capturing live video data of anatomical features of a patient;
identifying in the virtual model a virtual view based on the received tracking information and the particular location within the patient, wherein the identified virtual view corresponds to the user's view of the patient;
rendering, by executing software instructions on a computer system, a virtual image from the virtual model based on the identified virtual view at the particular location within the patient;
communicating the rendered virtual image to a display where the rendered virtual image is combined with the live video of the anatomical features of the patient and the user's view to form an augmented reality view of the patient that is displayed by said display;
receiving an input from the user to move the particular location to an arbitrary new location within the patient;
identifying in the virtual model an updated virtual view based on the received tracking information and the new location within the patient, wherein the updated virtual view corresponds to the user's current view of the patient;
rendering, by executing software instructions on the computer system, an updated virtual image from the virtual model based on the current virtual view at the new location within the patient; and
communicating the updated virtual image to the display where the updated virtual image is combined with the live video of the anatomical features of the patient and the user's current view to form an augmented reality view of the patient that is displayed by said display.

24. The method of claim 23, further comprising the steps of, in real time:
receive updated tracking information continuously from the position sensor as a user's position relative to the patient and the user's angle of view of the patient changes; and
identify virtual views corresponding to the updated tracking information such that the virtual views are continuously synchronized with the user's view of the patient.

25. The method of claim 23, further comprising the steps of:
receiving a live video feed from an endoscope camera corresponding to the user's view of the patient; and
generating, by executing software instructions on the computer system, an augmented reality view of the patient by continuously rendering in real time and combining virtual image with the live video feed, wherein the virtual image is synchronized with the live video feed based on the tracking information.

26. The method of claim 23, further comprising the steps of:
receiving second tracking information from a position sensor configured to directly detect a location or motion of the second user or a physical feature of the patient indicative of a second user's current view of the patient, including the second user's position relative to the patient and the second user's angle of view of the patient, wherein the second user's current view is different than the user's current view of the patient;
identifying in the virtual model a second virtual view based on the received second tracking information, wherein the identified second virtual view corresponds to the second user's view of the patient;
rendering, by executing software instructions on a computer system, a second virtual image from the virtual model based on the identified second virtual view; and
communicating the rendered second virtual image to a second display where the rendered second virtual image is combined with the second user's view to form a second augmented reality view of the patient, simultaneous to communicating the first rendered virtual image to the first display.

27. The method of claim 23, further comprising the step of receiving tracking information about a location of the patient or a part of the patient, wherein said augmented reality view is rendered using information about the location of the patient.

28. The method of claim 23, wherein the live video data of anatomical features of a patient are captured by an endoscope camera that is used on the patient to provide real-time patient organ data to support images in the augmented reality view.

29. The method of claim 28, wherein an image of said endoscope camera is included in said augmented reality view.

30. The method of claim 23, wherein said position sensor is mounted on a head mounted display worn by the user, and wherein said head mounted display provides a pass-through view of the patient to the user.

31. The method of claim 23, further comprising the step of generating a virtual avatar for display in the virtual three-dimensional image showing the current location of the user's perspective as the location changes.

32. The method of claim 31, wherein a virtual model marker is provided in the rendered virtual three dimensional image such that the marker is configured to perform an action when the avatar are within a predefine proximity of the marker.

33. The method of claim 23, wherein the perspective of the user inside the patient can be changed by operation of a controller.

34. The method of claim 23, wherein the perspective of the user inside the patient can be changed by a change of location of the user's position.

35. A virtual reality surgical navigation method, comprising the steps of:
preparing a multi dimension virtual model associated with an anatomy inside of a patient;
capturing live video data of anatomical features of the patient;
receiving position data indicative of a user's current head position from a position sensor, said position sensor configured to directly detect a location or motion of the user or a physical feature of the patient, said position data including direction of view and angle of view;
rendering, by executing software instructions on a computer system, an initial virtual three-dimensional image from the virtual model, the virtual three-dimensional image being representative of an anatomical view from an initial perspective at a particular location inside the patient, wherein the perspective is determined by data indicative of the user's current head position and the particular location, wherein
the anatomical views of the initial perspective at the first location can be changed by movement of the user's head to different directions of view;
communicating the initial rendered virtual image to a virtual headset display;
receiving data input indicative of the user's head moving to an updated position;
receiving an input from the user to move the particular location to an arbitrary new location within the patient; and
rendering, by executing software instructions on the computer system, an updated virtual three-dimensional image from the virtual model, the updated virtual three-dimensional image being representative of an anatomical view from an updated perspective at the new location inside the patient, wherein the updated perspective is determined by data indicative of the user's current head position and the input from the user about the new location, wherein
said second virtual three-dimensional image utilizes the live video data of anatomical features of the patient for generating said image, and wherein
the anatomical views of both the initial perspective at the first location and the updated perspective at the new location can be changed by movement of the user's head to different directions of view.

36. The method of claim 35, further comprising the steps of:
receiving data input indicative of the user's desire to view the inside of the patient from a second location; and
rendering, by executing software instructions on the computer system, a third virtual three-dimensional image from the virtual model, the third virtual three-dimensional image being representative of an anatomical view at the second location inside the patient as indicated by the received data.

37. The method of claim 35, further comprising:
continuously, in real time, receiving updated position data from the non-video sensor as a user's head position changes and desired location inside the patient changes; and
continuously, in real time, rendering virtual three-dimensional image being representative of an anatomical view from a perspective and location corresponding to the updated head position and updated location.

38. The method of claim 35, wherein the live video data of anatomical features of a patient are captured by an endoscope camera that is used on the patient to provide real-time patient organ data in said second virtual three-dimensional image.

39. The method of claim 38, wherein an image of said endoscope camera is included in said second virtual three-dimensional image.

40. The method of claim 35, wherein said position sensor is mounted on a head mounted display worn by the user, and wherein said head mounted display provides a pass-through view of the patient to the user.

41. The method of claim 35, further comprising the step of generating a virtual avatar for display in the virtual three-dimensional image showing the current location of the user's perspective as the location changes.

42. The method of claim 41, wherein a virtual model marker is provided in the rendered virtual three dimensional image such that the marker is configured to perform an action when the avatar are within a predefine proximity of the marker.

43. The method of claim 35, wherein the perspective of the user inside the patient can be changed by operation of a controller.

44. The method of claim 35, wherein the perspective of the user inside the patient can be changed by a change of location of the user's position.

45. A virtual reality surgical navigation method, comprising the steps of:
preparing a multi dimension virtual model associated with an anatomy inside of a patient;
receiving position data for a location within the patient;
receiving position data indicative of a user's current direction of view from a position sensor, said position sensor configured to directly detect a location or motion of the user or a physical feature of the patient, said position data including direction of view;
rendering, by executing software instructions on a computer system, an virtual three-dimensional image from the virtual model, the virtual three-dimensional image being representative of an anatomical view of the patient from the perspective at the location inside the patient, wherein the perspective is determined by data indicative of the user's current direction of view, wherein
the anatomical views of the initial perspective at the particular location can be changed by changing to different directions of view of the user;
receiving position data indicative of a change in the direction of view of the user;
rendering, by executing software instructions on the computer system, an updated virtual three-dimensional image from the virtual model, the updated virtual three-dimensional image being representative of an anatomical view from the location inside the patient, wherein the updated perspective is determined by the data indicative of the change in the direction of view;
integrating, into the virtual model in real-time, at least one avatar representative of the user's current relative position in the virtual model; and
integrating, into the virtual model a marker that is configured to perform an action responsive to determining that at least one of the at least one avatar is within a predefine proximity of the marker, wherein
the rendered virtual images are continuously provided to a virtual headset display for display to the user.

46. The method of claim 45, wherein the action includes changing colors within the virtual model.

47. The method of claim 45, wherein the action includes activating an audible alarm.

48. The method of claim 45, wherein the action includes displaying additional information in the display.

49. A virtual reality surgical navigation method, comprising the steps of:
obtaining medical images associated with anatomy inside a particular patient;
preparing a multi dimension virtual model from the medical images associated with the anatomy inside of the patient;
receiving position data for a particular location within the patient;
receiving position data indicative of a user's current direction of view from a position sensor, said position sensor configured to directly detect a location or motion of the user or a physical feature of the patient, said position data including direction of view;
rendering, by executing software instructions on a computer system, an initial virtual three-dimensional image from the virtual model, the virtual three-dimensional image being representative of an anatomical view of the patient from an initial perspective at the particular location inside the patient, wherein the perspective is determined by data indicative of the user's current direction of view and the particular location, wherein
the anatomical views of the initial perspective at the particular location can be changed by changing to different directions of view of the user;
receiving an input to move the particular location to an arbitrary new location within the patient;
rendering, by executing software instructions on the computer system, an updated virtual three-dimensional image from the virtual model, the updated virtual three-dimensional image being representative of an anatomical view from an updated perspective at the new location inside the patient, wherein the updated perspective is determined by data indicative of the user's current direction of view at the new location; and
generating a virtual avatar for display in the virtual three-dimensional image showing the current location of the user's perspective as the location changes, wherein
the anatomical views of the updated perspective at the new location can be changed by changing to different directions of view of the user, wherein
the rendered virtual images are continuously provided to a virtual headset display for display to the user, and wherein
a virtual model marker is provided in the rendered virtual three dimensional image such that the marker is configured to perform an action when the avatar are within a predefine proximity of the marker.

* * * * *